(12) United States Patent
Yang et al.

(10) Patent No.: US 11,348,258 B2
(45) Date of Patent: *May 31, 2022

(54) SYSTEM AND METHOD FOR REGISTERING MULTI-MODALITY IMAGES

(71) Applicant: SHANGHAI UNITED IMAGING HEALTHCARE CO., LTD., Shanghai (CN)

(72) Inventors: Gang Yang, Shanghai (CN); Miaoyan Du, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/945,943

(22) Filed: Aug. 3, 2020

(65) Prior Publication Data

US 2020/0410698 A1 Dec. 31, 2020

Related U.S. Application Data

(63) Continuation of application No. 16/023,322, filed on Jun. 29, 2018, now Pat. No. 10,733,746, which is a (Continued)

(30) Foreign Application Priority Data

Nov. 2, 2016 (CN) .......................... 201610971276.3

(51) Int. Cl.
*G06T 7/33* (2017.01)
*G06T 11/00* (2006.01)
(Continued)

(52) U.S. Cl.
CPC ............ *G06T 7/337* (2017.01); *A61B 5/0035* (2013.01); *A61B 5/7425* (2013.01);
(Continued)

(58) Field of Classification Search
CPC ......... G06T 7/337; G06T 11/008; G06T 7/74; G06T 7/50; G06T 3/0068; G06T 11/006;
(Continued)

(56) References Cited

U.S. PATENT DOCUMENTS 9,245,201 B1 * 1/2016 Jin ........................ G06K 9/6215
10,733,746 B2 * 8/2020 Yang .................... A61B 6/5235
(Continued)

FOREIGN PATENT DOCUMENTS

CN 102525525 A 7/2012
CN 103942772 A 7/2014
(Continued)

OTHER PUBLICATIONS

Liu, Zhoaxia , "A Simple and Robust Feature Point Matching Algorithm Based on Restricted Spatial Order Constraints for Aerial Image Registration", IEEE Transactions on Geoscience and Remote Sensing. (Year: 2012).*

(Continued)

*Primary Examiner* — Emily C Terrell
*Assistant Examiner* — Molly Delaney
(74) *Attorney, Agent, or Firm* — Metis IP LLC

(57) ABSTRACT

The present disclosure relates to a method and system for registering multi-modality images. The method may include: acquiring a first image relating to one or more reference objects; acquiring a second image relating to the one or more reference objects; determining a set of reference points based on the one or more reference objects; determining a set of mapping data corresponding to the set of reference points in the first image and the second image; and determining one or more registration parameters by comparing a plurality of back-projection errors generated in a plurality of iterations that are performed based on the set of mapping data.

20 Claims, 15 Drawing Sheets

Related U.S. Application Data continuation of application No. PCT/CN2017/108649, filed on Oct. 31, 2017.

(51) Int. Cl.
*G06T 7/73* (2017.01)
*G06T 7/50* (2017.01)
*A61B 6/00* (2006.01)
*A61B 5/00* (2006.01)
*G06T 3/00* (2006.01)
*A61B 5/055* (2006.01)
*A61B 6/03* (2006.01)
*G06T 3/20* (2006.01)
*G06T 3/60* (2006.01)

(52) U.S. Cl.
CPC .......... *A61B 6/5235* (2013.01); *A61B 6/5247* (2013.01); *G06T 3/0068* (2013.01); *G06T 7/50* (2017.01); *G06T 7/74* (2017.01); *G06T 11/006* (2013.01); *G06T 11/008* (2013.01); *A61B 5/055* (2013.01); *A61B 5/743* (2013.01); *A61B 6/035* (2013.01); *A61B 6/037* (2013.01); *G06T 3/20* (2013.01); *G06T 3/60* (2013.01); *G06T 2207/10081* (2013.01); *G06T 2207/10088* (2013.01); *G06T 2207/10104* (2013.01); *G06T 2211/421* (2013.01); *G06T 2211/424* (2013.01)

(58) Field of Classification Search
CPC ... G06T 3/20; G06T 3/60; G06T 2207/10088; G06T 2211/421; G06T 2211/424; G06T 2207/10081; G06T 2207/10104; G06T 11/003; G06T 2207/10072; A61B 6/5247; A61B 6/5235; A61B 5/7425; A61B 5/0035; A61B 5/055; A61B 6/035; A61B 6/037; A61B 5/743
See application file for complete search history.

(56) References Cited

U.S. PATENT DOCUMENTS

| | | | |
|---|---|---|---|
| 2006/0217925 A1* | 9/2006 | Taron | G06K 9/6206 702/179 |
| 2008/0260220 A1 | 10/2008 | Djeziri | |
| 2014/0193053 A1* | 7/2014 | Kadoury | G06T 15/08 382/131 |
| 2015/0009214 A1* | 1/2015 | Lee | G06T 17/20 345/420 |
| 2017/0301099 A1* | 10/2017 | Otomaru | G06T 7/251 |
| 2017/0325689 A1* | 11/2017 | Salah | G06T 7/251 |
| 2017/0337682 A1* | 11/2017 | Liao | G06T 7/30 |
| 2018/0268547 A1* | 9/2018 | Miyasa | G06T 7/97 |
| 2018/0308245 A1 | 10/2018 | Yang et al. | |
| 2019/0350680 A1* | 11/2019 | Chekh | A61C 7/002 |

FOREIGN PATENT DOCUMENTS

| | | |
|---|---|---|
| CN | 104504705 A | 4/2015 |
| CN | 104700451 A | 6/2015 |
| CN | 104732529 A | 6/2015 |
| CN | 104732540 A | 6/2015 |

OTHER PUBLICATIONS

International Search Report in PCT/CN2017/108649 dated Jan. 25, 2018, 4 pages.

Written Opinion in PCT/CN2017/108649 dated Jan. 25, 2018, 5 pages.

Liu Zhaoxia et al., A Simple and Robust Feature Point Matching Algorithm Based on Restricted Spatial Order Constraints for Aerial Image Registration, IEEE Transactions on Geoscience and Remote Sensing, 50(2): 514-527, 2012.

* cited by examiner

SYSTEM AND METHOD FOR REGISTERING MULTI-MODALITY IMAGES

CROSS-REFERENCE TO RELATED APPLICATIONS

This application is a continuation of U.S. patent application Ser. No. 16/023,322 filed on Jun. 29, 2018, which is a continuation of International Application No. PCT/CN2017/108649 filed on Oct. 31, 2017, which claims priority to Chinese Application No. 201610971276.3 filed on Nov. 2, 2016, the entire contents of which are hereby incorporated by reference.

TECHNICAL FIELD

The present disclosure generally relates to image processing, and more particularly, a system and method for registering multi-modality images based on a registration model.

BACKGROUND

Multi-modality imaging systems may generate one or more functional images and one or more structural images. For example, a PET-CT system may generate a functional PET image and a structural CT image. One or more lesion locations may be determined accurately based on a registration of the functional image(s) and corresponding structural image(s). The images generated by a multi-modality imaging system may provide more detailed and reliable diagnostic information than that generated by a single-modality system (e.g., a CT system, a PET system, an MRI system, etc.). However, there may be an error in the reconstruction centers of a functional image and a structural image generated by a multi-modality imaging system. The error of reconstruction center may reduce registration accuracy. Therefore, it is desirable to correct the error of the reconstruction centers of the multi-modality imaging systems.

SUMMARY

According to an aspect of the present disclosure, a method is provided. The method may include one or more of the following operations. A processor may acquire a first image relating to a registration model, wherein the registration model includes a plurality of reference objects. The processor may acquire a second image relating to the registration model. The processor may determine a set of reference points based on the plurality of reference objects, the set of reference points including a plurality of first reference points, wherein the plurality of first reference points include at least two first reference points, and the distance between the at least two first reference points represents the shortest distance between two of the plurality of reference objects. The processor may determine a set of mapping data corresponding to the set of reference points in the first image and the second image, the set of mapping data reflecting a mapping relation between a first coordinate position of at least one reference point of the set of reference points in the first image and a second coordinate position of the at least one reference point in the second image. Furthermore, the processor may determine one or more registration parameters based on the set of mapping data.

According to another aspect of the present disclosure, a system is provided. The system may include at least one non-transitory computer-readable storage medium and at least one processor. The at least one storage medium may include a set of instructions. When the at least one processor execute the set of instructions, the at least one processor may be configured to perform one or more of the following operations. The at least one processor may acquire a first image relating to a registration model, wherein the registration model includes a plurality of reference objects. The at least one processor may acquire a second image relating to the registration model. The at least one processor may determine a set of reference points based on the plurality of reference objects, the set of reference points including a plurality of first reference points, wherein the plurality of first reference points includes at least two first reference points, and the distance between the at least two first reference points represents the shortest distance between two of the plurality of reference objects. The at least one processor may determine a set of mapping data corresponding to the set of reference points in the first image and the second image, the set of mapping data reflecting a mapping relation between a first coordinate position of at least one reference point of the set of reference points in the first image and a second coordinate position of the at least one reference point in the second image. The at least one processor may determine one or more registration parameters based on the set of mapping data.

According to a further aspect of the present disclosure, a non-transitory computer readable medium is provided. The non-transitory computer readable medium may include executable instructions that, when executed by at least one processor, cause the at least one processor to effectuate a method. The method may include one or more of the following operations. The computing device may acquire a second image relating to the registration model. The computing device may determine a set of reference points based on the plurality of reference objects, the set of reference points including a plurality of first reference points, wherein the plurality of first reference points includes at least two first reference points, and the distance between the at least two first reference points represents the shortest distance between two of the plurality of reference objects. The computing device may determine a set of mapping data corresponding to the set of reference points in the first image and the second image, the set of mapping data reflecting a mapping relation between a first coordinate position of at least one reference point of the set of reference points in the first image and a second coordinate position of the at least one reference point in the second image. The computing device may determine one or more registration parameters based on the set of mapping data.

According to a further aspect of the present disclosure, a system is provided. The system may have at least one processor and a storage configured to store instructions. The system may include: an acquisition module configured to acquire a first image relating to a registration model and a second image relating to the registration model, wherein the registration model includes a plurality of reference objects; a reference object determination unit configured to determine a set of reference points based on the plurality of reference objects, the set of reference points including a plurality of first reference points, wherein the plurality of first reference points include at least two first reference points, and the distance between the at least two first reference points represents the shortest distance between two of the plurality of reference objects; a mapping data determination unit configured to determine a set of mapping data corresponding to the set of reference points in the first image and the second image, the set of mapping data reflecting a mapping relation between a first coordinate position of at least one reference point of the set of reference points in the first image and a second coordinate position of the at least one reference point in the second image; and a registration parameter determination unit configured to determine one or more registration parameters based on the set of mapping data.

In some embodiments, the processor may determine a plurality of characteristic points of the plurality of reference objects. The processor may determine the plurality of reference objects in the first image based on the plurality of characteristic points. The processor may determine the plurality of reference objects in the second image based on the plurality of characteristic points.

In some embodiments, the processor may determine a plurality of characteristic points of the plurality of reference objects according to the following operations. The processor may determine a plurality of intersection points between at least three parallel planes and the plurality of reference objects. The processor may designate the plurality of intersection points as the plurality of characteristic points.

In some embodiments, the processor may determine the plurality of reference objects in the first image according to the following operations. The processor may acquire a first plurality of coordinate positions of the plurality of characteristic points in the first image. The processor may determine a first plurality of slopes corresponding to the plurality of reference objects based on the first plurality of coordinate positions. The processor may further determine a first location distribution of the plurality of reference objects in the first image based on the first plurality of slopes and the first plurality of coordinate positions.

In some embodiments, the processor may determine a first plurality of slopes of the plurality of reference objects according to the following operations. The processor may determine at least one slope based on every two of the plurality of characteristic points to obtain a first set of slopes. The processor may divide the first set of slopes into a plurality of groups based on values of the first set of slopes, wherein one or more slopes in each group are substantially the same. The processor may determine determining one or more target groups that have a maximum number of slopes. The processor may designate one or more values of the one or more target groups as the first plurality of slopes corresponding to the plurality of reference objects.

In some embodiments, the processor may determine a first location distribution of the plurality of reference objects in the first image according to the following operations. The processor may determine a distance between every two reference objects in the first image. The processor may determine the first location distribution of the plurality of reference objects in the first image based on the distances determined for the plurality of reference objects in the first image.

In some embodiments, the processor may determine the plurality of reference objects in the second image according to the following operations. The processor may acquire a second plurality of coordinate positions of the plurality of characteristic points in the second image. The processor may determine a second plurality of slopes corresponding to the plurality of reference objects based on the second plurality of coordinate positions. The processor may determine a second location distribution of the plurality of reference objects in the second image based on the second plurality of slopes and the second plurality of coordinate positions.

In some embodiments, the processor may determine a second plurality of slopes of the plurality of reference objects according to the following operations. The processor may determine at least one slope based on every two of the plurality of characteristic points to obtain a second set of slopes. The processor may divide the second set of slopes into a plurality of groups based on values of the second set of slopes, wherein one or more slopes in each group are substantially the same. The processor may determine one or more target groups that have a maximum number of slopes. The processor may designate one or more values of the one or more target groups as the second plurality of slopes corresponding to the plurality of reference objects.

In some embodiments, the processor may determine a second location distribution of the plurality of reference objects in the second image according to the following operations. The processor may determine a distance between every two reference objects in the second image. The processor may determine the second location distribution of the plurality of reference objects in the second image based on the distances determined for the plurality of reference objects in the second image.

In some embodiments, the processor may determine the plurality of second reference points based on the plurality of first reference points, wherein one of the plurality of second reference points and one of the plurality of first reference points that belong to a same reference object of the plurality of reference objects have a specific distance.

In some embodiments, the processor may determine a set of mapping data corresponding to the set of reference points in the first image and the second image according to the following operations. The processor may determine a first set of mapping data corresponding to the plurality of first reference points, the first set of mapping data reflecting a mapping relation between a third coordinate position of at least one first reference point of the plurality of first reference points in the first image and a fourth coordinate position of the at least one first reference point in the second image. The processor may determine a second set of mapping data corresponding to the plurality of second reference points, the second set of mapping data reflecting a mapping relation between a fifth coordinate position of at least one second reference point of the plurality of second reference points in the first image and a sixth coordinate position of the at least one second reference point in the second image.

In some embodiments, the one or more registration parameters include a rotation matrix and a translation vector.

In some embodiments, the processor may determine the one or more registration parameters by comparing a plurality of back-projection errors generated in a plurality of iterations.

In some embodiments, the plurality of iterations is performed based on a Random Sample Consensus algorithm.

In some embodiments, the plurality of reference objects include a plurality of skew lines on different planes.

In some embodiments, the registration model including the plurality of skew lines on different planes may be constructed.

In some embodiments, the first image may be a computer tomography image or a magnetic resonance image.

In some embodiments, the second image may be a positron emission tomography image.

In some embodiments, the first image may be obtained by a first imaging device, and the second image may be obtained by a second imaging device.

In some embodiments, the first image may be obtained by a first portion of a multi-modality imaging device, and the second image may be obtained by a second portion of the multi-modality imaging device.

In some embodiments, the plurality of first reference points may include a first point and a second point, and the distance between the first point and the second point represents the shortest distance between two portions of one of the plurality of reference objects.

In some embodiments, the processor may further register a third image and a fourth image based on the one or more registration parameters.

In some embodiments, the reference object determination unit may include a characteristic point determination subunit configured to determine a plurality of characteristic points of the plurality of reference objects. The reference object determination unit may be further configured to determine the plurality of reference objects in the first image based on the plurality of characteristic points and determine the plurality of reference objects in the second image based on the plurality of characteristic points.

In some embodiments, the characteristic point determination subunit may be further configured to determine a plurality of intersection points between at least three parallel planes and the plurality of reference objects, and designate the plurality of intersection points as the plurality of characteristic points.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by another expression if they achieve the same purpose.

Figure 2:
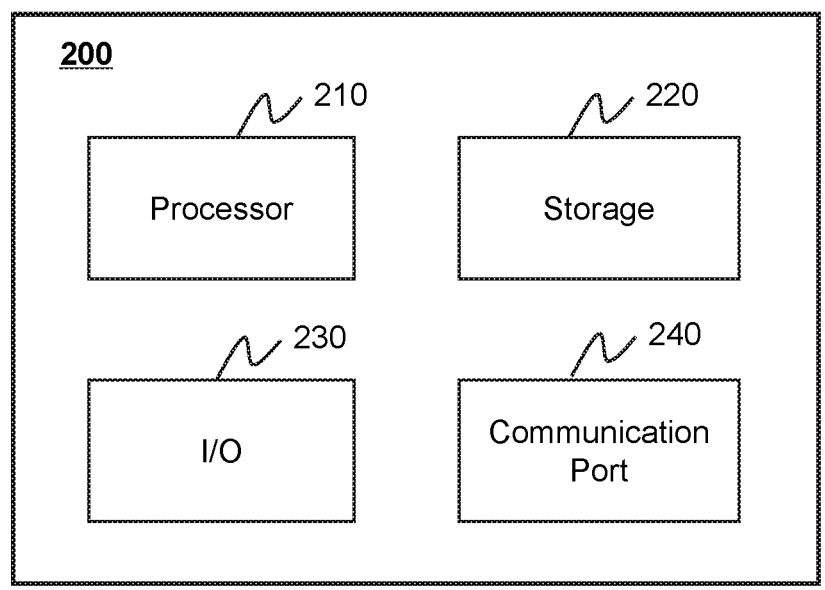
FIG. 2 is a schematic diagram illustrating exemplary hardware and/or software components of an exemplary computing device on which the processing engine may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

In some embodiments, the imaging system may include one or more modalities including Digital Subtraction Angiography (DSA), Magnetic Resonance Imaging (MRI), Magnetic Resonance Angiography (MRA), Computed tomography (CT), Computed Tomography Angiography (CTA), Ultrasound Scanning (US), Positron Emission Tomography (PET), Single-Photon Emission Computerized Tomography (SPECT), CT-MR, CT-PET, CE-SPECT, DSA-MR, PET-MR, PET-US, SPECT-US, TMS (transcranial magnetic stimulation)-MR, US-CT, US-MR, X-ray-CT, X-ray-MR, X-ray-portal, X-ray-US, Video-CT, Vide-US, or the like, or any combination thereof. In some embodiments, a subject to be scanned by the imaging system may be an organ, a texture, a lesion, a tumor, a substance, or the like, or any combination thereof. Merely by way for example, the subject may include a head, a breast, a lung, a rib, a vertebra, a trachea, a pleura, a mediastinum, an abdomen, a long intestine, a small intestine, a bladder, a gallbladder, a triple warmer, a pelvic cavity, a backbone, extremities, a skeleton, a blood vessel, or the like, or any combination thereof. As another example, the subject may include a physical model. In some embodiments, the image generated by the imaging system may include a 2D image and/or a 3D image. In the 2D image, its tiniest distinguishable element may be termed as a pixel. In the 3D image, its tiniest distinguishable element may be termed as a voxel ("a volumetric pixel" or "a volume pixel"). In some embodiments, the 3D image may also be seen as a series of 2D slices or 2D layers.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The following description is provided with reference to an image processing technique for registering multi-modality images. It is understood that this is not intended to limit the scope of the present disclosure. For persons having ordinary skills in the art, a certain amount of variations, changes and/or modifications may be deducted under guidance of the present disclosure. Those variations, changes and/or modifications do not depart from the scope of the present disclosure.

Figure 1:
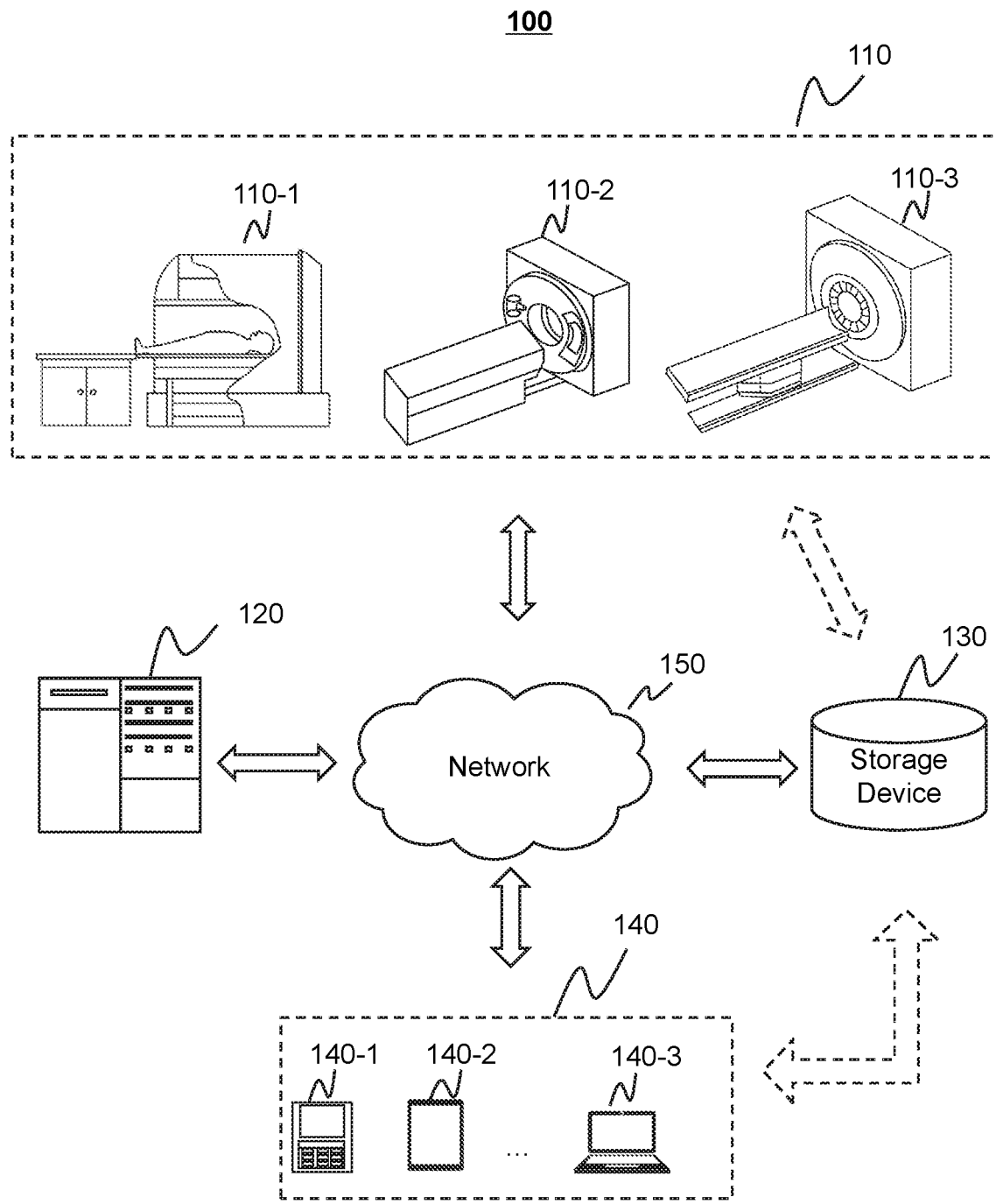
FIG. 1 is a schematic diagram illustrating an exemplary imaging system according to some embodiments of the present disclosure.

FIG. 1 is a schematic diagram illustrating an exemplary imaging system 100 according to some embodiments of the present disclosure. As shown, the imaging system 100 may include a scanner 110, a processing device 120, a storage device 130, one or more terminals 140, and a network 150. The components in the imaging system 100 may be connected in one or more of various ways. Merely by way of example, as illustrated in FIG. 1, the scanner 110 may be connected to the processing device 120 through the network 150. As another example, the scanner 110 may be connected to the processing device 120 directly as indicated by the bi-directional arrow in dotted lines linking the scanner 110 and the processing device 120. As a further example, the storage device 130 may be connected to the processing device 120 directly or through the network 150. As still a further example, one or more terminals 140 may be connected to the processing device 120 directly (as indicated by the bi-directional arrow in dotted lines linking the terminal 140 and the processing device 120) or through the network 150.

The scanner 110 may generate or provide image data via scanning a subject or a part of the subject. In some embodiments, the scanner 110 may be a medical imaging device, for example, a PET device, a SPECT device, a CT device, an MRI device, or the like, or any combination thereof (e.g., a PET-CT device, a PET-MRI device, etc.). In some embodiments, the scanner 110 may include a single-modality scanner. The single-modality scanner may include, for example, a magnetic resonance imaging (MRI) scanner 110-1, a computed tomography (CT) scanner 110-2, and/or a positron emission tomography (PET) scanner 110-3. In some embodiments, the scanner 110 may include both the CT scanner 110-2 and the PET scanner 110-3. In some embodiments, image data of different modalities related to the subject, such as CT image data and PET image data, may be acquired using different scanners separately. In some embodiments, the scanner 110 may include a multi-modality scanner. The multi-modality scanner may include a positron emission tomography-computed tomography (PET-CT) scanner, a positron emission tomography-magnetic resonance imaging (PET-MRI) scanner, or the like, or any combination thereof. The multi-modality scanner may perform multi-modality imaging simultaneously. For example, the PET-CT scanner may generate structural X-ray CT image data and functional PET image data simultaneously in a single scan. The PET-MRI scanner may generate MRI data and PET data simultaneously in a single scan.

In some embodiments, the subject may include a body, a substance, or the like, or any combination thereof. In some embodiments, the subject may include a specific portion of a body, such as a head, a thorax, an abdomen, or the like, or any combination thereof. In some embodiments, the subject may include a specific organ, such as an esophagus, a trachea, a bronchus, a stomach, a gallbladder, a small intestine, a colon, a bladder, a ureter, a uterus, a fallopian tube, etc. In some embodiments, the subject may include a physical model (also referred to as a mockup). The physical model may include one or more materials constructed as different shapes and/or dimensions. Different parts of the physical model may be made of different materials. Different materials may have different X-ray attenuation coefficients, different tracer isotopes, and/or different hydrogen proton contents. Therefore, different parts of the physical model may be recognized by the imaging system 100. In the present disclosure, "object" and "subject" are used interchangeably. In some embodiments, the scanner 110 may include a scanning table. The subject may be placed on the scanning table for imaging.

In some embodiments, the scanner 110 may transmit the image data via the network 150 to the processing device 120, the storage device 130, and/or the terminal(s) 140. For example, the image data may be sent to the processing device 120 for further processing, or may be stored in the storage device 130.

The processing device 120 may process data and/or information obtained from the scanner 110, the storage device 130, and/or the terminal(s) 140. For example, the processing device 120 may determine one or more registration parameters for registering two or more multi-modality images based on the image data collected by the scanner 110. In some embodiments, the processing device 120 may be a single server or a server group. The server group may be centralized or distributed. In some embodiments, the processing device 120 may be local or remote. For example, the processing device 120 may access information and/or data from the scanner 110, the storage device 130, and/or the terminal(s) 140 via the network 150. As another example, the processing device 120 may be directly connected to the scanner 110, the terminal(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be implemented by a computing device 200 having one or more components as described in connection with FIG. 2.

The storage device 130 may store data, instructions, and/or any other information. In some embodiments, the storage device 130 may store data obtained from the scanner 110, the processing device 120, and/or the terminal(s) 140. In some embodiments, the storage device 130 may store data and/or instructions that the processing device 120 may execute or use to perform exemplary methods described in the present disclosure. In some embodiments, the storage device 130 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform as described elsewhere in the disclosure. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the imaging system 100 (e.g., the processing device 120, the terminal(s) 140, etc.). One or more components in the imaging system 100 may access the data or instructions stored in the storage device 130 via the network 150. In some embodiments, the storage device 130 may be part of the processing device 120.

The terminal(s) 140 may be connected to and/or communicate with the scanner 110, the processing device 120, and/or the storage device 130. For example, the terminal(s) 140 may obtain a processed image from the processing device 120. As another example, the terminal(s) 140 may obtain image data acquired by the scanner 110 and transmit the image data to the processing device 120 to be processed. In some embodiments, the terminal(s) 140 may include a mobile device 140-1, a tablet computer 140-2, a laptop computer 140-3, or the like, or any combination thereof. For example, the mobile device 140-1 may include a mobile phone, a personal digital assistance (PDA), a gaming device, a navigation device, a point of sale (POS) device, a laptop, a tablet computer, a desktop, or the like, or any combination thereof. In some embodiments, the terminal(s) 140 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing device 120 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 140 may be part of the processing device 120.

The network 150 may include any suitable network that can facilitate exchange of information and/or data for the imaging system 100. In some embodiments, one or more components of the imaging system 100 (e.g., the scanner 110, the processing device 120, the storage device 130, the terminal(s) 140, etc.) may communicate information and/or data with one or more other components of the imaging system 100 via the network 150. For example, the processing device 120 may obtain image data from the scanner 110 via the network 150. As another example, the processing device 120 may obtain user instruction(s) from the terminal(s) 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, witches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the imaging system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage device 130 may be a data storage including cloud computing platforms, such as, public cloud, private cloud, community, and hybrid clouds, etc. However, those variations and modifications do not depart from the scope of the present disclosure.

FIG. 2 is a schematic diagram illustrating exemplary hardware and/or software components of an exemplary computing device 200 on which the processing device 120 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 210 may process image data obtained from the scanner 110, the terminal(s) 140, the storage device 130, and/or any other component of the Imaging system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the scanner 110, the terminal(s) 140, the storage device 130, and/or any other component of the Imaging system 100. In some embodiments, the storage 220 may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 120 for determining one or more registration parameters related to multi-modality images acquired by the imaging system 100.

The I/O 230 may input and/or output signals, data, information, etc. In some embodiments, the I/O 230 may enable a user interaction with the processing device 120. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 150) to facilitate data communications. The communication port 240 may establish connections between the processing device 120 and the scanner 110, the terminal(s) 140, and/or the storage device 130. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or any combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
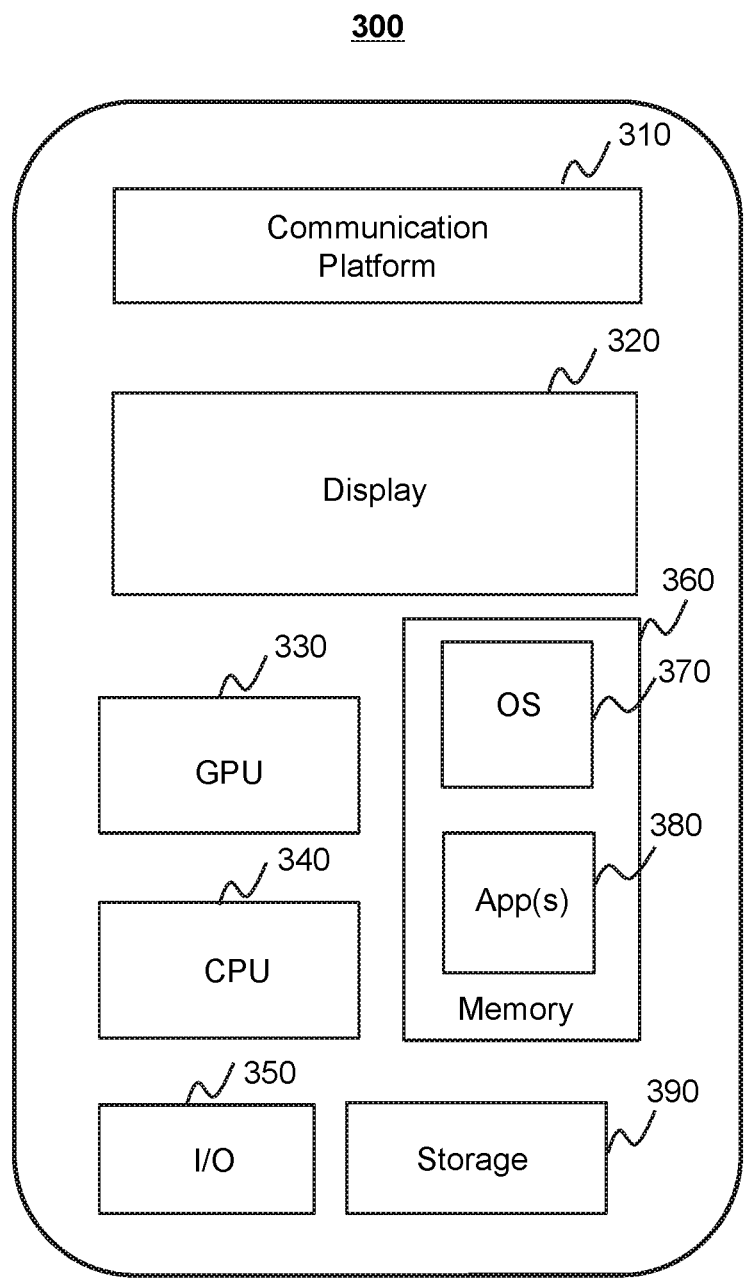
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device 300 on which the terminal(s) 140 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information respect to image processing or other information from the processing device 120. User interactions with the information stream may be achieved via the I/O 350 and provided to the processing device 120 and/or other components of the imaging system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or external device. A computer may also act as a server if appropriately programmed.

Figure 4:
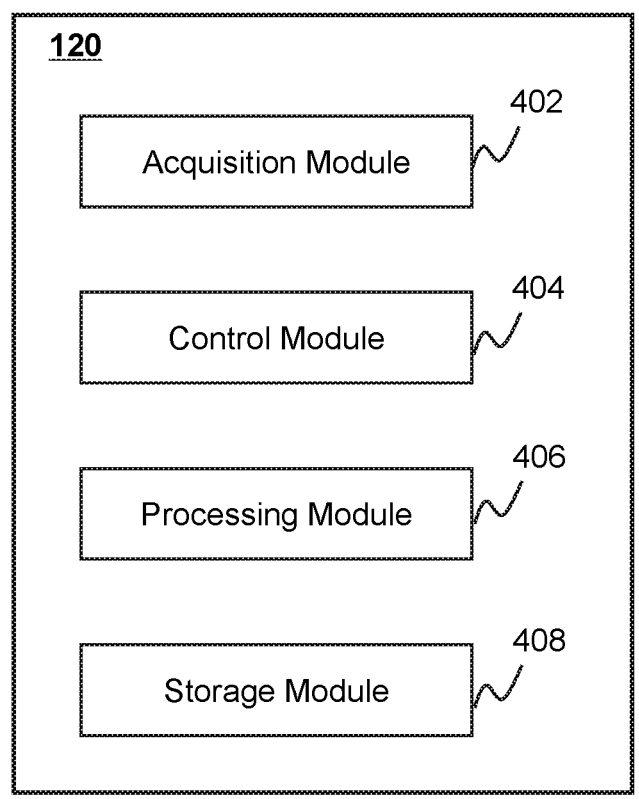
FIG. 4 is a block diagram illustrating an exemplary processing device according to some embodiments of the present disclosure.

FIG. 4 is a block diagram illustrating an exemplary processing device 120 according to some embodiments of the present disclosure. The processing device 120 may include an acquisition module 402, a control module 404, a processing module 406, and a storage module 408. At least a portion of the processing device 120 may be implemented on a computing device as illustrated in FIG. 2 or a mobile device as illustrated in FIG. 3.

The acquisition module 402 may acquire image data. The acquisition module 402 may acquire the image data from the scanner 110, the storage device 130, and/or the terminal(s) 140. In some embodiments, the acquisition module 402 may acquire the image data from an external data source via the network 150. In some embodiments, the image data may correspond to X-rays that pass through a subject. In some embodiments, a radioactive scanning source may emit the X-rays to the subject. The X-rays may pass through the subject and may attenuate during the passing-through. The extent of attenuation of an X-ray may depend on factors including, for example, the property of the subject the X-ray passes through, the thickness of the subject that the X-ray passes through, etc. The attenuated X-rays may be detected by a detector and transmitted to the acquisition module 402. In some embodiments, the image data may be generated based on one or more radiation rays (e.g., γ rays) that emit from the subject. In some embodiments, the image data may be generated based on magnetic resonance imaging. The acquisition module 402 may acquire image data at various times, via various devices, and/or under various conditions (e.g., weather, illuminance, scanning position and angle, etc.). In some embodiments, the acquisition module 402 may acquire instructions for processing the image data. The instructions may be executed by the processor(s) of the processing device 120 to perform exemplary methods described in this disclosure. In some embodiments, the acquired data may be transmitted to the storage module 408 to be stored.

The control module 404 may control operations of the acquisition module 402, the storage module 408, the processing module 406 (e.g., by generating one or more control parameters), the scanner 110, or the like, or a combination thereof. For example, the control module 404 may control the acquisition module 402 to acquire image data, the timing of the acquisition of the image data, etc. As another example, the control module 404 may control the processing module 406 to process image data acquired by the acquisition module 402. As a further example, the control module 404 may control the operation of the scanner 110. In some embodiments, the control module 404 may receive a real-time instruction from an operator or retrieve a predetermined instruction provided by a user (e.g., a doctor, a technician, an engineer, etc.) to control one or more operations of the scanner 110, the acquisition module 402, and/or the processing module 406. For example, the control module 404 may adjust the acquisition module 402 and/or the processing module 406 to generate one or more images of a subject according to the real-time instruction and/or the predetermined instruction. In some embodiments, the control module 404 may communicate with one or more other modules of the processing device 120 for exchanging information and/or data.

The processing module 406 may process information provided by various modules of the processing device 120. The processing module 406 may process image data acquired by the acquisition module 402, image data retrieved from the storage module 408 and/or the storage device 130, etc. In some embodiments, the processing module 406 may reconstruct one or more images based on the image data according to a reconstruction technique, generate reports including one or more images and/or other related information, and/or perform any other function for image reconstruction in accordance with various embodiments of the present disclosure. The reconstruction technique may include an iterative reconstruction algorithm (e.g., a statistical reconstruction algorithm), a Fourier slice theorem algorithm, a filtered back projection (FBP) algorithm, a fan-beam reconstruction algorithm, an analytic reconstruction algorithm, or the like, or any combination thereof. In some embodiments, the processing module 406 may reduce or remove artifacts and/or noise in iterative reconstruction. In some embodiments, the processing module 406 may register multi-modality images. For example, the processing module 406 may register a CT image and a PET image. As another example, the processing module 406 may register an MRI image and a PET image. In some embodiments, the processing module 406 may register multi-modality images based on one or more registration techniques. Exemplary registration techniques may include an intensity-based technique, an area-based technique, a feature-based technique, or the like, or any combination thereof. It should be understood that, for the persons having ordinary skills in the art, the same or similar registration techniques may be suitable. All such suitable registration techniques are within the protection scope of the present disclosure.

The storage module 408 may store image data, control parameters, processed image data, or the like, or a combination thereof. In some embodiments, the storage module 408 may store one or more programs and/or instructions that may be executed by the processor(s) of the processing device 120 to perform exemplary methods described in this disclosure. For example, the storage module 408 may store program(s) and/or instruction(s) that can be executed by the processor(s) of the processing device 120 to acquire image data, reconstruct an image based on the image data, register two or more images, and/or display any intermediate result or a resultant image.

In some embodiments, one or more modules illustrated in FIG. 4 may be implemented in at least part of the exemplary imaging system 100 as illustrated in FIG. 1. For example, the acquisition module 402, the control module 404, the processing module 406, and/or the storage module 408 may be integrated into a console (not shown). Via the console, a user may set the parameters for scanning a subject, controlling imaging processes, controlling the parameters for image reconstruction, adjusting the parameters for registering multi-modality images, etc. In some embodiments, the console may be implemented via the processing device 120 and/or the terminal(s) 140.

Figure 5:
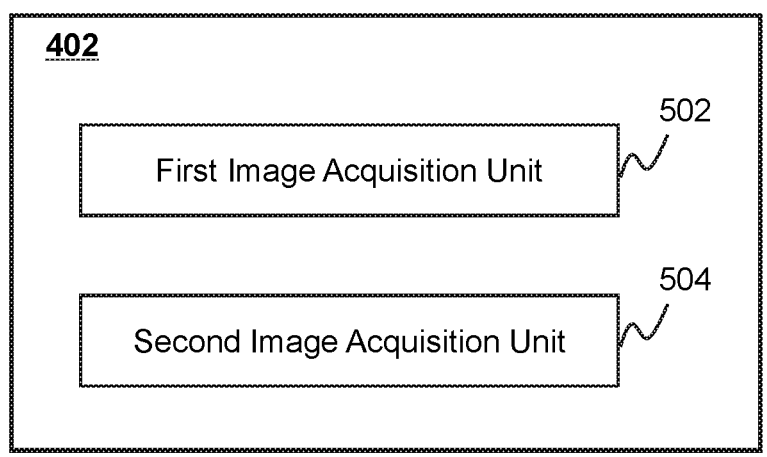
FIG. 5 is a block diagram illustrating an exemplary acquisition module according to some embodiments of the present disclosure.

FIG. 5 is a block diagram illustrating an exemplary acquisition module 402 according to some embodiments of the present disclosure. The acquisition module 402 may include a first image acquisition unit 502 and a second image acquisition unit 504. At least a portion of the acquisition module 402 may be implemented on a computing device 200 as illustrated in FIG. 2 or a mobile device 300 as illustrated in FIG. 3.

The first image acquisition unit 502 may acquire a first image (also referred to herein as a first modality image). The first image may refer to a first modality image of a registration model. The first image may be a structural image or a functional image relating to the registration model. For example, the first modality image may include a CT image and/or an MRI image relating to the registration model. More descriptions of the registration model may be found elsewhere in the present disclosure. See, for example, FIG. 6 and the description thereof. The first image acquisition unit 502 may acquire the first image from the scanner 110, the storage device 130, and/or the terminal(s) 140. In some embodiments, the first image acquisition unit 502 may acquire the first image from an external data source (not shown) via the network 150. In some embodiments, the first image acquisition unit 502 may transmit the first image to the processing module 406 for further processing.

The second image acquisition unit 504 may acquire a second image (also referred to herein as a second modality image). The second image may refer to a second modality image of the registration model. The second image may be a functional image or a structural image relating to the registration model. In some embodiments, the modality of the second image may be different from that of the first image. In some embodiments, the second image and the first image may relate to a same registration model. For example, the second modality image may include a PET image relating to the same registration model as the first modality image. The first image and the second image relating to the same registration model may be generated simultaneously or sequentially. It should be noted that when the first image and the second image are generated, a position of the registration model relative to the scanning table may remain unchanged. More descriptions of the registration model may be found elsewhere in the present disclosure. See, for example, FIG. 6 and the description thereof. The second image acquisition unit 504 may acquire the second image from the scanner 110, the storage device 130, and/or the terminal(s) 140. In some embodiments, the second image acquisition unit 504 may acquire the second image from an external data source via the network 150. In some embodiments, the second image acquisition unit 504 may transmit the second image to the processing module 406 for further processing.

It should be noted that the above description of the acquisition module 402 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the acquisition module 402 may further include a third image acquisition unit, a fourth image acquisition unit, etc.

Figure 6:
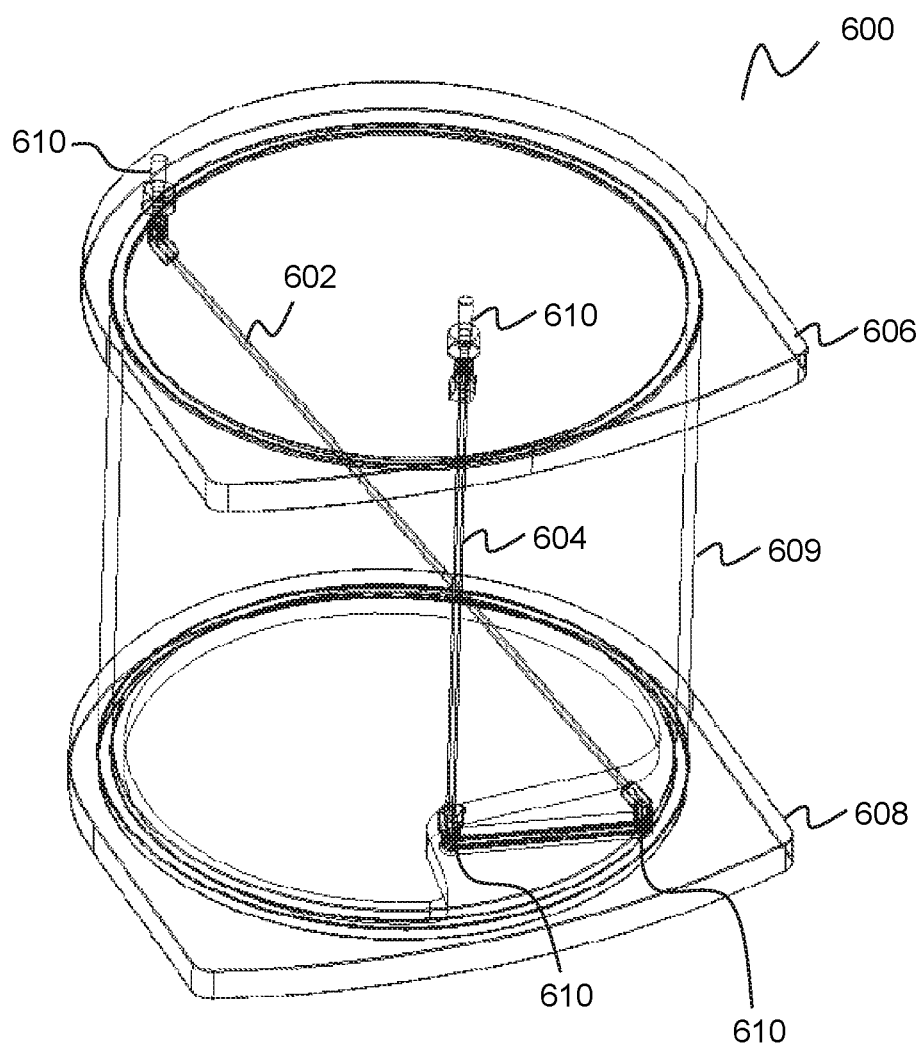
FIG. 6 is a schematic diagram illustrating an exemplary registration model according to some embodiments of the present disclosure.

FIG. 6 is schematic diagram illustrating an exemplary registration model 600 according to some embodiments of the present disclosure. In some embodiments, the registration model may be a test phantom. The registration model may include one or more reference objects. The reference objects may include one or more specific materials so that the reference objects may be easily recognized in one or more images generated by scanning the registration model. In some embodiments, a reference object may include a container (e.g., a vessel) and one or more imaging agents. The container may be transparent or opaque. The container may be made of any suitable material, for example, glass, metal, plastic, ceramic, polymer, or the like, or any combination thereof. For example, the container may be a tubular container (e.g., a slim tube), a spherical vessel, a flask, etc. In some embodiments, the imaging agent may refer to a radioactive trace. Exemplary imaging agents may include $^{18}$F-FDG, $^{18}$F-FLT, $^{18}$F-FES, $^{18}$F-FMISO, $^{11}$C-Methionline, $^{11}$C-Choline, etc. For persons having ordinary skills in the art, any suitable imaging agent may be applied to fill in a reference object. Besides, the reference objects may be designed in various shapes and/or dimensions. Exemplary shapes may include a cylindrical shape, a globular shape, a cuboid shape, a cube shape, a cone shape, or the like, or any combination thereof. The dimension of a reference object may relate to a spatial resolution of the scanner 110, a sensitivity of the scanner 110, a dimension of a scanning channel of the scanner 110, an axial field of view (FOV) of the scanner 110, etc. For example, if a reference object include a slim tube, the diameter of the slim tube may be 1 cm, 2 cm, etc.

As shown in FIG. 6, the exemplary registration model 600 may include a first reference object 602, a second reference object 604. In some embodiments, the registration model 600 may further include a third reference object (not shown), a fourth reference object (not shown), etc. In some embodiments, for the convenience of fixation of the reference objects, the registration model 600 may further include a first cover plate 606, a second cover plate 608, and/or a shell 609. In some embodiments, the registration model 600 may have a shape of cylinder. The first cover plate 606, the second cover plate 608, and/or the shell 609 may be transparent or opaque. The materials of the first cover plate 606, the second cover plate 608, and/or the shell 609 may be the same as of different from the reference objects. In some embodiments, the second cover plate 608 (or the first cover plate 606) and the shell 609 may be configured as an integral piece. In some embodiments, the first cover plate 606, the second cover plate 608, and/or the shell 609 may include one or more fixing devices 610 to fix the reference objects. The fixing device(s) 610 may connect the reference objects, the first cover plate 606, the second cover plate 608, and/or the shell 609 by way of overlapping, mortise, occlusion, engagement, or the like, or any combination thereof. In some embodiments, the connection between the reference objects, the first cover plate 606, the second cover plate 608, and/or the shell 609 may be detachable. For example, the detachable connection may be a threaded fastener connection. In a threaded fastener connection, the stationary installation 610 may include one or more bolts and/or nuts. In some embodiments, the residual space inside the registration model 600 excluding the reference objects may be filled with other materials different from that of the reference objects. In some embodiments, the residual space may be filled with a gas (e.g., air). In some embodiments, the residual space may be a vacuum. In some embodiments, the reference object(s) may include no imaging agent, and the residual space may include one or more imaging agents, so that the reference object(s) may be differentiated from a background in an image generated by scanning the registration model 600. For example, for magnetic resonance imaging, the reference object(s) may include no imaging agent, and the residual space may include sodium sulfate.

In some embodiments, the reference objects may be placed in different planes in the registration model. For example, as illustrated in FIG. 6, if the first reference object 602 and the second reference object 604 are constructed as straight slim tubes, the first reference object 602 and the second reference object 604 may be regarded as two skew lines on different planes. In some embodiments, the reference object(s) may include one or more curves on different planes, or one or more space curves.

In some embodiments, a reference object (e.g., the first reference object 602, the second reference object 604, etc.) may include one or more reference points. The reference point(s) may be marked or constructed in the corresponding reference object. For example, the container of the reference object may include a node that is isolated from other parts of the reference object, and the node may contain an imaging agent that is different from other parts of the reference object, so that a reference point corresponding to the node may be generated in an image.

It should be noted that the above description of the registration model 600 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the registration model may include a reference object of other shapes, such as a vertebrae, a cube, etc. In some embodiments, the registration model 600 may be a commercial product available in the market. The number of the reference objects may be any integer equal to or larger than 1.

Figure 7:
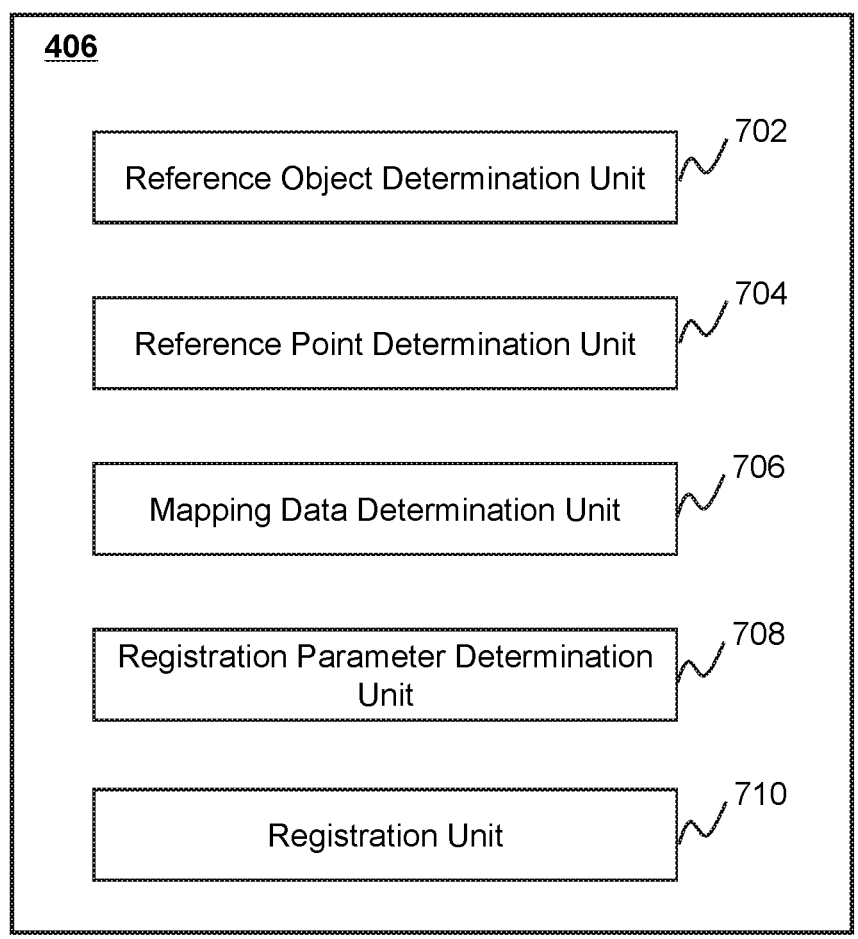
FIG. 7 is a block diagram illustrating an exemplary processing module according to some embodiments of the present disclosure.

FIG. 7 is a block diagram illustrating an exemplary processing module 406 according to some embodiments of the present disclosure. The processing module 406 may include a reference object determination unit 702, a reference point determination unit 704, a mapping data determination unit 706, a registration parameter determination unit 708, and a registration unit 710. The processing module 406 may be implemented on various components (e.g., the processor 210 of the computing device 200 as illustrated in FIG. 2). At least a portion of the processing module 406 may be implemented on the computing device 200 as illustrated in FIG. 2 or a mobile device 300 as illustrated in FIG. 3.

The reference object determination unit 702 may determine one or more reference objects of the registration model. In some embodiments, the reference objects may include one or more skew lines on different planes (e.g., the first reference object 602, the second reference object 604, as illustrated in FIG. 6). In some embodiments, the reference object determination unit 706 may determine one or more location distributions of the reference objects. In some embodiments, the reference object determination unit 702 may determine the reference objects based on one or more coordinate positions of one or more points in an image (e.g., a first image, a second image, etc.) relating to the registration model. For example, if the reference objects are skew lines on different planes, the reference object determination unit 706 may determine the location distribution of the reference objects based on the slope of each skew line and a coordinate position of at least one point in each skew line.

The reference point determination unit 704 may determine one or more reference points of the reference object(s). The reference point may refer to a point at a certain position in a reference object. In some embodiments, the certain position of the reference point in a reference object may relate to another reference object. In some embodiments, the reference point determination unit 704 may determine the reference point(s) based on the reference object(s). In some embodiments, a reference object may include one or more reference points. In some embodiments, a reference point in a first reference object may correspond to another reference point in a second reference object. In some embodiments, the reference point determination unit 704 may determine the positions of the reference points in two reference objects based on a relative position of the two reference objects. For example, the reference point determination unit 704 may determine one or more first reference points based on a shortest distance between every two reference objects. As another example, the reference point determination unit 704 may determine one or more second reference points based on the already determined first reference point(s).

The mapping data determination unit 706 may determine mapping data corresponding to the reference points. The mapping data of a point may include information regarding a first coordinate position of the point in a first image and a second coordinate position of the point in a second image. The mapping data may reflect a mapping relation between the first coordinate positions of the reference points in the first image and the second coordinate positions of the reference points in the second image. In some embodiments, the mapping data determination unit 706 may determine the first coordinate positions of the reference points (e.g., the points $P_{10}$ and $P_{20}$ shown in FIG. 11) in the first image and the second coordinate positions of the same reference points (e.g., the points $P_{10}$ and $P_{20}$ shown in FIG. 11) in the second image. The mapping data determination unit 706 may transmit the determined mapping data to one or more other units of the processing module 406 for further processing.

The registration parameter determination unit 708 may determine one or more registration parameters based on the mapping data. The registration parameter may be used to register a first image (e.g., a CT image, a MRI image, etc.) and a second image (e.g., a PET image, etc.). In some embodiments, the registration parameters may include a rotation matrix and a translation vector. A rotation matrix may include one or more (e.g., three) rotation parameters relating to rotation of a point of a reference object (or a pixel/voxel of an image) in one or more (e.g., three) directions. A translation vector may include one or more (e.g., three) translation parameters relating to translation of a point of a reference object (or a pixel/voxel of an image) in one or more (e.g., three) directions. In some embodiments, the registration parameter determination unit 708 may determine the registration parameter(s) according to one or more algorithms. Exemplary algorithm may include a random sample consensus (RANSAC) algorithm, an iterative closest point (ICP) algorithm, a residual histogram analysis (RHA) algorithm, a J-Linkage algorithm, a kernel fitting algorithm, a gradient-based algorithm, a fast decent algorithm, etc. In some embodiments, the registration parameter determination unit 708 may transmit the determined registration parameter(s) to the registration unit 710 for registering multi-modality images.

The registration unit 710 may register two or more images relating to a subject based on the determined registration parameter(s). In some embodiments, the subject may be a human body, or a portion of the human body (e.g., an organ, a texture, a lesion, a tumor, etc.). The two or more images (e.g., a third image, a fourth image, etc.) may have different modalities. For example, the third image may include a CT image and/or an MRI image relating to the subject, the fourth image may include a PET image relating to the same subject.

It should be noted that the description of the processing module 406 is provided for the purposes of illustration, and not intended to limit the scope of the present disclosure. For persons having ordinary skills in the art, various variations and modifications may be conducted under the teaching of the present disclosure. However, those variations and modifications do not depart from the scope of the present disclosure. For example, the reference object determination unit 702 may be integrated into the reference point determination unit 704, or the mapping data determination unit 706. As another example, the registration parameter determination unit 708 may be integrated into the registration unit 710.

Figure 8:
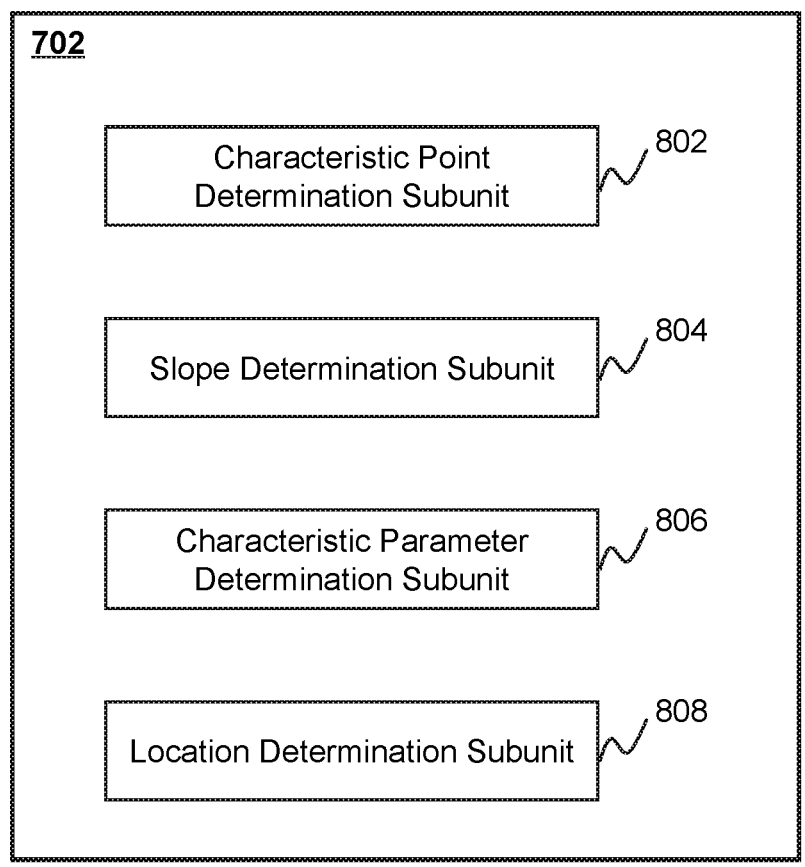
FIG. 8 is a block diagram illustrating an exemplary reference object determination unit according to some embodiments of the present disclosure.

FIG. 8 is a block diagram illustrating an exemplary reference object determination unit 702 according to some embodiments of the present disclosure. The reference object determination unit 702 may include a characteristic point determination subunit 802, a slope determination subunit 804, a characteristic parameter determination subunit 806, and a location determination subunit 808. At least a portion of the reference object determination unit 702 may be implemented on a computing device 200 as illustrated in FIG. 2 or a mobile device 300 as illustrated in FIG. 3.

The characteristic point determination subunit 802 may determine one or more characteristic points of the reference object(s). A characteristic point may refer to a point at a characteristic position in a reference object. In some embodiments, the characteristic position may refer to an intersection position of a reference object and an auxiliary plane or auxiliary line. In some embodiments, the characteristic point determination subunit 802 may determine the characteristic point at the intersection position. For example, if the reference objects include two skew lines on different planes, the characteristic point determination subunit 802 may determine one or more intersection points between two or more (e.g., at least three) parallel auxiliary planes and the reference objects. The intersection points may be designated as the characteristic points. In some embodiments, the characteristic point determination subunit 802 may transmit the corresponding coordinate positions of the characteristic points to the slope determination subunit 804 for further processing.

The slope determination subunit 804 may determine one or more slopes of the reference object(s) based on the coordinate position(s) of the characteristic point(s). In some embodiments, the slope determination subunit 804 may determine a slope of a line defined by every two characteristic points based on the coordinate positions of the two characteristic points. The slope determination subunit 804 may determine a first set of slopes based on the coordinate positions of the characteristic points in a first image. The slope determination subunit 804 may determine a second set of slopes based on the coordinate positions of the characteristic points in a second image. The slope determination subunit 804 may divide the first set of slopes into a plurality of groups based on the values of the first set of slopes. The slope determination subunit 804 may divide the second set of slopes into a plurality of groups based on the values of the second set of slopes. One or more slopes in each group may be substantially the same. The slope determination subunit 804 may determine one or more target groups that have a maximum number of slopes. The values of the target groups may be designated as the slopes corresponding to the reference objects.

The characteristic parameter determination subunit 806 may determine one or more characteristic parameters (e.g., distances) relating to the reference object(s). A characteristic parameter relating to the reference object(s) may be a parameter that may be used to determine a relative position of the reference object(s). In some embodiments, the characteristic parameter may be a distance (e.g., a shortest distance) between every two reference objects. In some embodiments, a common vertical line of every two reference objects may have two intersection points with the every two reference objects, and the distance between the two intersection points may represent a characteristic parameter relating to the every two reference objects. In some embodiments, the characteristic parameter determination subunit 806 may transmit the characteristic parameters to the location determination subunit 808 for determining a location distribution of the reference objects.

The location determination subunit 808 may determine one or more location distributions of the reference object(s). In some embodiments, the location determination subunit 808 may determine the location distributions of the reference objects based on one or more points (e.g., the characteristic points or reference points in the reference objects) and one or more slopes of the reference objects. In some embodiments, the location determination subunit 808 may determine the location distributions based on the determined reference objects and/or the characteristic parameters (e.g., the shortest distance between every two reference objects). For example, the location determination subunit 808 may determine the location distribution of the first reference object in the first image based on the coordinate positions of two characteristic points of the first reference object and/or a first slope of the first reference object, and determine the location distribution of the second reference object in the first image based on the location distribution of the first reference object and the shortest distance between the first reference object and the second reference object. In some embodiments, the location determination subunit 808 may adjust or correct the location distributions based on the determined characteristic parameter(s).

It should be noted that the description of the reference object determination unit 702 is provided for the purposes of illustration, and not intended to limit the scope of the present disclosure. For persons having ordinary skills in the art, various variations and modifications may be conducted under the teaching of the present disclosure. However, those variations and modifications do not depart from the scope of the present disclosure. For example, the characteristic parameter determination subunit 806 may be integrated into the location determination subunit 808.

Figure 9:
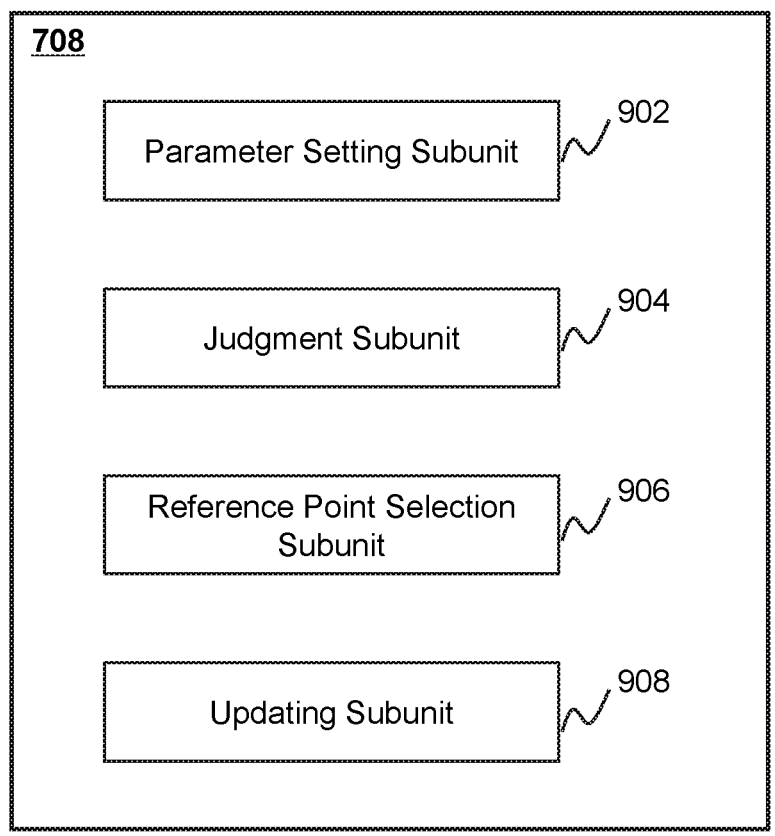
FIG. 9 is a block diagram illustrating an exemplary registration parameter determination unit according to some embodiments of the present disclosure.

FIG. 9 is a block diagram illustrating an exemplary registration parameter determination unit 708 according to some embodiments of the present disclosure. The registration parameter determination unit 708 may include a parameter setting subunit 902, a judgment subunit 904, a reference point selection subunit 906, and an updating subunit 908. At least a portion of the registration parameter determination unit 708 may be implemented on a computing device 200 as illustrated in FIG. 2 or a mobile device 300 as illustrated in FIG. 3.

The parameter setting subunit 902 may set one or more parameters. The parameters may include a number of sample points, a maximum number of iterations, a current iteration count, a current set of points, an initial value for a registration parameter, an initial value for a back-projection error, a first threshold, a second threshold, etc. More descriptions of the parameters may be found elsewhere in the present disclosure. See, for example, FIG. 15 and the description thereof. In some embodiments, the number of sample points may refer to a minimum number of sample points (e.g., 3, 4, 5, 6, etc.) for determining the registration parameters. The maximum number of iterations may be an integer larger than 1 (e.g., 50, 100, 1000, etc.). The current iteration count may be an integer larger than 0. The current set of points may include all or a portion of the reference points. The parameter setting subunit 902 may determine the initial value for a registration parameter based on the mapping data relating to one or more (e.g., all) reference points in the current set of points. The parameter setting subunit 902 may determine the initial value of the back-projection error based on the initial registration parameter and one or more (e.g., all) reference points in the current set of points. In some embodiments, the parameter setting subunit 902 may set one or more parameters associated with the RANSAC algorithm. In some embodiments, the parameter setting subunit 902 may set the parameter(s) based on one or more default values. The default values may be determined by the imaging system 100, or may be preset by a user or operator via the terminal(s) 140.

The judgment subunit 904 may judge one or more parameters relating to intermediate results generated by the implementation of the processing module 406. In some embodiments, the intermediate results may include a current iteration count, a point number of a current set of points, a current back-projection error, etc. In some embodiments, the judgment subunit 904 may judge whether the intermediate result(s) satisfy a condition. The condition may be determined based on a user input, or a default setting of the imaging system 100. For example, the judgment subunit 904 may judge whether a certain number of iterations have been performed. In some embodiments, the judgment subunit 904 may transmit the judgment result to other subunits of the registration parameter determination unit 708 (e.g., the reference point selection subunit 906, the updating subunit 908, etc.). In some embodiments, the processing module 406 may determine whether to terminate iteration based on the judgment result of the judgment subunit 904.

The reference point selection subunit 906 may select one or more sample points from the reference points in the current set of points. In some embodiments, the reference point selection subunit 906 may select the sample points randomly or sequentially. In some embodiments, the reference point selection subunit 906 may transmit the selected sample points to the updating subunit 908 to update one or more parameters (e.g., the registration parameter, etc.).

The updating subunit 908 may update one or more parameters. The parameters to be updated may relate to intermediate results generated by the implementation of the processing module 406. For example, the updating subunit 908 may update the current set of points, the number of the current set of points, the first threshold, the second threshold, the current iteration count, and/or the registration parameter. The updating subunit 908 may update the parameters based on the judgment result of the judgment subunit 904. In some embodiments, the updating subunit 908 may update the parameters during each iteration. The updating subunit 908 may transmit the updated parameters to other subunits of the registration parameter determination unit 708 (e.g., the judgment subunit 904, the reference point selection subunit 906, etc.) for further processing.

Figure 10:
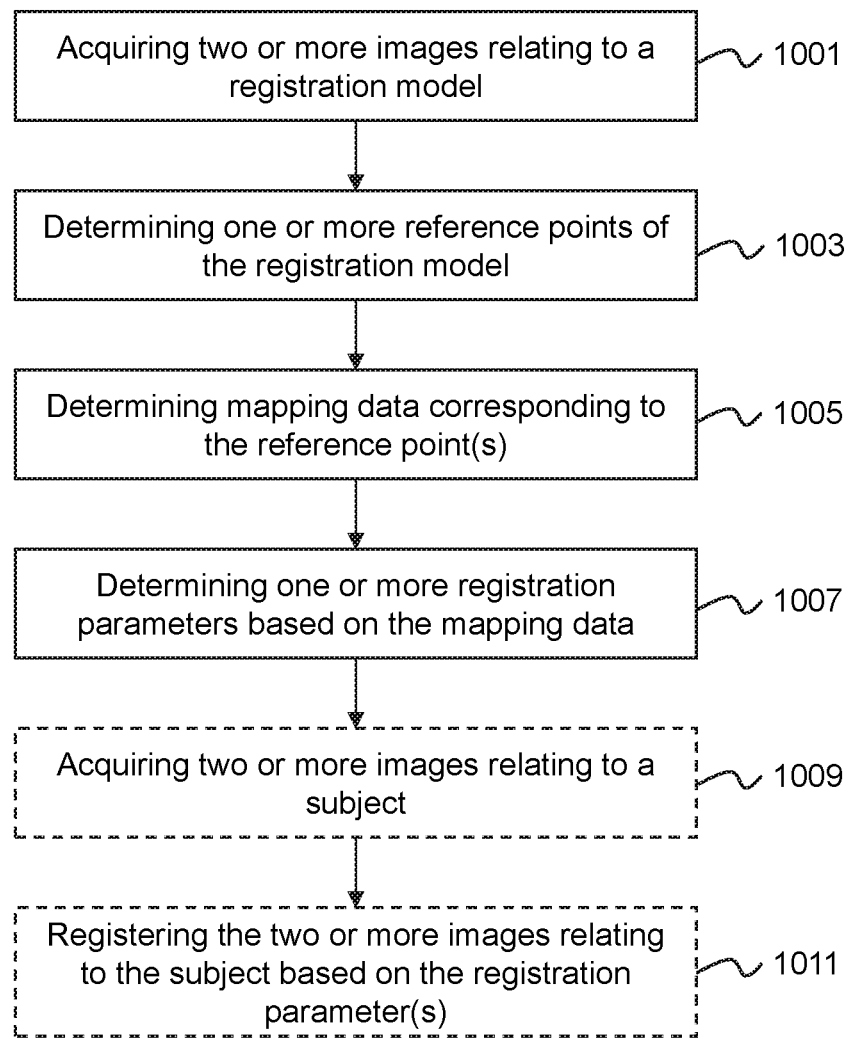
FIG. 10 is a flowchart illustrating an exemplary process for registering two or more images according to some embodiments of the present disclosure.

FIG. 10 is a flowchart illustrating an exemplary process 1000 for registering two or more images according to some embodiments of the present disclosure. In some embodiments, one or more operations of process 1000 illustrated in FIG. 10 for registering two or more images may be implemented in the imaging system 100 illustrated in FIG. 1. For example, the process 1000 illustrated in FIG. 10 may be stored in the storage device 130 in the form of instructions, and invoked and/or executed by the processing device 120 (e.g., the processor 210 of the computing device 200 as illustrated in FIG. 2, the CPU 340 of the mobile device 300 as illustrated in FIG. 3). As another example, a portion of the process 1000 may be implemented on the scanner 110. The operations of the illustrated process presented below are intended to be illustrative. In some embodiments, the process may be accomplished with one or more additional operations not described, and/or without one or more of the operations discussed. Additionally, the order in which the operations of the process as illustrated in FIG. 10 and described below is not intended to be limiting.

In 1001, two or more images relating to a registration model (e.g., the registration model illustrated in FIG. 6) may be acquired. Operation 1001 may be performed by the acquisition module 402. The images may be 3D images. The images acquired in 1001 may include one or more first images, one or more second images, etc. In some embodiments, the images acquired in 1001 (e.g., a first image, a second image, etc.) may have different modalities. For example, the first image(s) may include a CT image and/or an MR image relating to the registration model. As another example, the second image(s) may include a PET image relating to the registration model. In some embodiments, the images may be generated sequentially or simultaneously. The images may be generated in different single-modality imaging devices or in a multi-modality imaging device. The registration model may include one or more reference objects. In some embodiments, the images may be acquired from the scanner 110, the storage device 130, the terminal 140, and/or an external data source.

In 1003, one or more reference points of the registration model may be determined. Operation 1003 may be performed by the reference point determination unit 704. In some embodiments, the reference point(s) may be determined based on the reference object(s) (e.g., each reference object) of the registration model. A reference point may refer to a point at a certain position in a reference object. In some embodiments, a reference object may include one or more reference points. In some embodiments, a reference point in a first reference object may correspond to another reference point in a second reference object. In some embodiments, every two reference objects of the registration model may have one or more corresponding reference points. In some embodiments, the positions of the reference points in two different reference objects may be determined based on a relative position of the two reference objects. For example, one or more first reference points may be determined based on a shortest distance between two reference objects. In some embodiments, one or more second reference points may be determined based on the already determined first reference point(s). For example, one or more points that have one or more specific distances from the already determined reference point(s) may be determined as reference point(s). The specific distance(s) may be default value(s) determined by the imaging system 100, or may be preset by a user or operator via the terminal(s) 140. In some embodiments, the reference point(s) may be arbitrarily selected in the reference object(s) of the registration model.

Figure 11:
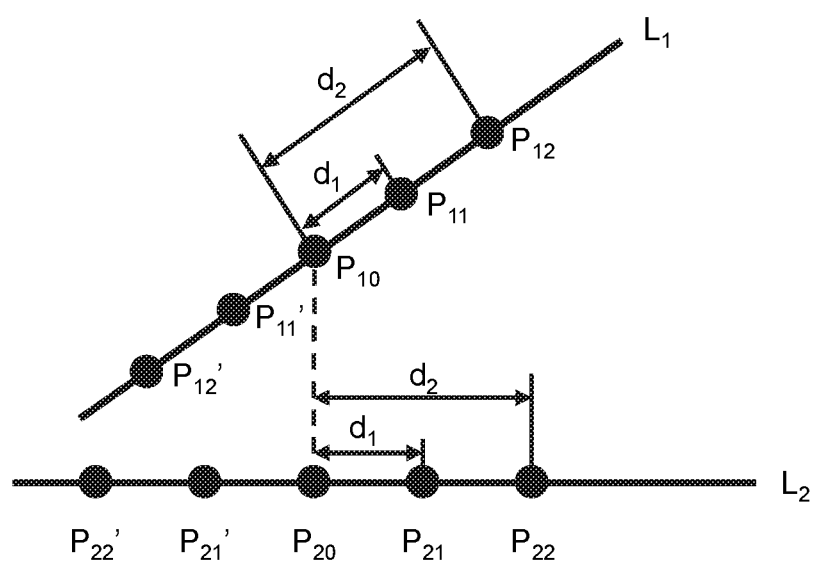
FIG. 11 is a schematic diagram illustrating one or more exemplary reference points according to some embodiments of the present disclosure.

Merely byway of example, the reference points determined in 1003 may include one or more first reference points and/or one or more second reference points. The first reference points may be determined based on a relative position of the reference objects. The second reference points may be determined based on the first reference points. In some embodiments, the reference points may include at least two first reference points. The distance between the at least two first reference points may represent the shortest distance between two reference objects. For example, as illustrated in FIG. 11, if two of the reference objects are skew lines on different planes, a common vertical line of the two skew lines may have two intersection points with the two skew lines, the distance between the two intersection points may represent the shortest distance between the two skew lines, and the two intersection points may be designated as the first reference points. In some embodiments, a second reference point may be determined based on a specific distance from a corresponding first reference point. More descriptions of the second reference points may be found elsewhere in the present disclosure. See, for example, FIG. 11 and the description thereof.

In 1005, mapping data corresponding to the reference points determined in 1003 may be determined. Operation 1005 may be performed by the mapping data determination unit 706. Mapping data of a point may include information regarding a first coordinate position of the point in a first image and a second coordinate position of the point in a second image. In some embodiments, a point in an object may correspond to a pixel or voxel in an image. The mapping data corresponding to the reference points may include information regarding a plurality of first coordinate positions of the reference points in a first image and a plurality of second coordinate positions of the reference points in a second image. The mapping data may reflect a mapping relation between the plurality of first coordinate positions of the reference points in the first image and the plurality of second coordinate positions of the reference points in the second image. For example, the mapping data determination unit 706 may determine the first coordinate positions of the first reference points (e.g., the points $P_{10}$ and $P_{20}$ shown in FIG. 11) in the first image and the second coordinate positions of the same first reference points (e.g., the points $P_{10}$ and $P_{20}$ shown in FIG. 11) in the second image. As another example, the mapping data determination unit 706 may determine the third coordinate positions of the second reference points (e.g., the points $P_{11}$, $P_{12}$, $P_{21}$, and $P_{22}$ shown in FIG. 11) in the first image and the fourth coordinate positions of the same second reference points (e.g., the points $P_{11}$, $P_{12}$, $P_{21}$, and $P_{22}$ shown in FIG. 11) in the second image. In some embodiments, the first image may be a CT image or an MR image relating to the registration model. In some embodiments, the second image may be a PET image relating to the same registration model.

In 1007, one or more registration parameters may be determined based on the mapping data determined in 1005. Operation 1007 may be performed by the registration parameter determination unit 708. The registration parameters may be used to register a first image (e.g., a CT image, an MR image, etc.) and a second image (e.g., a PET image, etc.). In some embodiments, the registration parameters may include a rotation matrix and a translation vector. A rotation matrix may include one or more (e.g., three) rotation parameters relating to rotation of a point of a reference object (or a pixel/voxel of an image) in one or more (e.g., three) directions. A translation vector may include one or more (e.g., three) translation parameters relating to translation of a point of a reference object (or a pixel/voxel of an image) in one or more (e.g., three) directions. Merely by way of example, in a three-dimensional Cartesian coordinate system, the rotation matrix may include three rotation parameters relating to rotation of a point in three directions (e.g., an X axis direction, a Y axis direction, and a Z axis direction), and the translation vector may include three translation parameters relating to translation of the point in three directions (e.g., the X axis direction, the Y axis direction, and the Z axis direction). Using the rotation parameters and the translation parameters, a pixel/voxel in a first image may be registered with a corresponding pixel/voxel in a second image.

In some embodiments, the registration parameters may be determined using one or more algorithms. Exemplary algorithms for determining registration parameters may include a random sample consensus (RANSAC) algorithm, an iterative closest point (ICP) algorithm, a residual histogram analysis (RHA) algorithm, a J-Linkage algorithm, a kernel fitting algorithm, a gradient-based algorithm, a fast decent algorithm, etc.

In 1009, two or more images relating to a subject may be acquired. Operation 1009 may be performed by the acquisition module 402. In some embodiments, the subject may be a human body, or a portion of the human body (e.g., an organ, a texture, a lesion, a tumor, etc.). The images acquired may include one or more third images and one or more fourth images. In some embodiments, the images acquired in 1009 (e.g., a third image, a fourth image, etc.) may have different modalities. For example, the third image(s) may include a CT image and/or an MR image relating to the subject. As another example, the fourth image(s) may include a PET image relating to the subject. In some embodiments, the images may be acquired sequentially in different single-modality imaging devices, or simultaneously in a multi-modality imaging device. In some embodiments, the first image and the third image may be generated by a same or similar imaging device. In some embodiments, the second image and the fourth image may be generated by a same or similar imaging device. In some embodiments, the images may be acquired from the scanner 110, the storage device 130, the terminal 140, and/or an external data source.

In 1011, the two or more images relating to the subject may be registered based on the registration parameter(s) determined in 1007. Operation 1011 may be performed by the registration unit 710. In some embodiments, one or more reference pixels/voxels may be determined in a third image, and then a fourth image may be registered with the third image based on the coordinate positions of the reference pixels/voxels in the third image and the registration parameter(s). In some embodiments, the reference pixels/voxels may be determined randomly. In some embodiments, the reference pixels/voxels may be determined based on a portion of the subject (e.g., a border of the subject, a center of the subject, etc.). Merely by way of example, a matrix corresponding to the coordinate positions of the reference pixels/voxels in the third image may be multiplied by a rotation matrix of the registration parameter(s) and then added to a translation vector of the registration parameter(s), and thus, the third image and the fourth image may be registered.

It should be noted that the description of the process 1000 is provided for the purposes of illustration, and not intended to limit the scope of the present disclosure. For persons having ordinary skills in the art, various variations and modifications may be conducted under the teaching of the present disclosure. However, those variations and modifications do not depart from the scope of the present disclosure. For example, operation 1003 and operation 1005 may be integrated into one single operation. As another example, operation 1001 and operation 1009 may be integrated into one single operation. As a further example, operation 1009 and/or operation 1011 may be omitted. In some embodiments, the first image and/or the third image may be a PET image. In some embodiments, the second image and/or the fourth image may be a CT image or an MR image.

FIG. 11 is a schematic diagram illustrating one or more exemplary reference points according to some embodiments of the present disclosure. Merely by way of example, a registration model may include one or more skew lines on different planes (also referred to herein as the reference objects). Two exemplary skew lines $L_1$ and $L_2$ on different planes are shown in FIG. 11 for the purpose of illustration. The skew lines $L_1$ and $L_2$ may have one or more first reference points. A common vertical line (e.g., the dashed line shown in FIG. 11) of the two skew lines $L_1$ and $L_2$ may have two intersection points (i.e., the point $P_{10}$ on line $L_1$ and the point $P_{20}$ on line $L_2$). The distance between the two intersection points $P_{10}$ and $P_{20}$ may represent the shortest distance between the two skew lines $L_1$ and $L_2$. The two intersection points $P_{10}$ and $P_{20}$ may be determined as the first reference points.

In some embodiments, one or more second reference points may be determined based on one or more specific distances from the first reference points. For example, the second reference point $P_{11}$ (or $P_{11}'$) on line $L_1$ may be determined based on a first specific distance (e.g., $d_1$) from the first reference point $P_{10}$. As another example, the second reference point $P_{21}$ (or $P_{21}'$) on line $L_2$ may be determined based on the first specific distance (e.g., $d_1$) from the first reference point $P_{20}$. As a further example, the second reference point $P_{12}$ (or $P_{12}'$) on line $L_1$ may be determined based on a second specific distance (e.g., $d_2$) from the first reference point $P_{10}$. As still a further example, the second reference point $P_{22}$ (or $P_{22}'$) on line $L_2$ may be determined based on the second specific distance (e.g., $d_2$) from the first reference point $P_{20}$. In some embodiments, the second specific distance may be different from the first specific distance. For example, the second specific distance may be two times as large as the first specific distance. In some embodiments, the first specific distance and/or the second specific distance may be default value(s) determined by the imaging system 100, or may be preset by a user or operator via the terminal(s) 140.

It should be noted that for persons having ordinary skills in the art, a plurality of reference points may be determined by the same or similar ways. For example, other second reference points not shown in FIG. 11 may be determined based on a third specific distance from the first reference points $P_{10}$ and $P_{20}$, respectively. As another example, if there are three skew lines $L_1$, $L_2$, and $L_3$, then a first reference point $P_{10}$ on line $L_1$, a first reference point $P_{20}$ on line $L_2$, a first reference point $P_{13}$ on line $L_1$, a first reference point $P_{31}$ on line $L_3$, a first reference point $P_{23}$ on line $L_2$, and/or a first reference point $P_{32}$ on line $L_3$ may be determined. The first reference point $P_{10}$ on line $L_1$ and the first reference point $P_{20}$ on line $L_2$ may represent the shortest distance between the two skew lines $L_1$ and $L_2$. The first reference point $P_{13}$ on line $L_1$ and the first reference point $P_{31}$ on line $L_3$ may represent the shortest distance between the two skew lines $L_1$ and $L_3$. The first reference point $P_{23}$ on line $L_2$ and the first reference point $P_{32}$ on line $L_3$ may represent the shortest distance between the two skew lines $L_2$ and $L_3$. Accordingly, a plurality of second reference points may be determined based on the first reference points $P_{10}$, $P_{20}$, $P_{13}$, $P_{31}$, $P_{23}$, and $P_{32}$. The number of skew lines may be any integer larger than 1, for example, 2, 3, 4, 5, ..., N, etc. N may be an integer larger than 1. In some embodiments, two first reference points may be determined based on a shortest distance between every two skew lines. Therefore, there may be $C_N^2$ first reference points for N skew lines on different planes.

Figure 12:
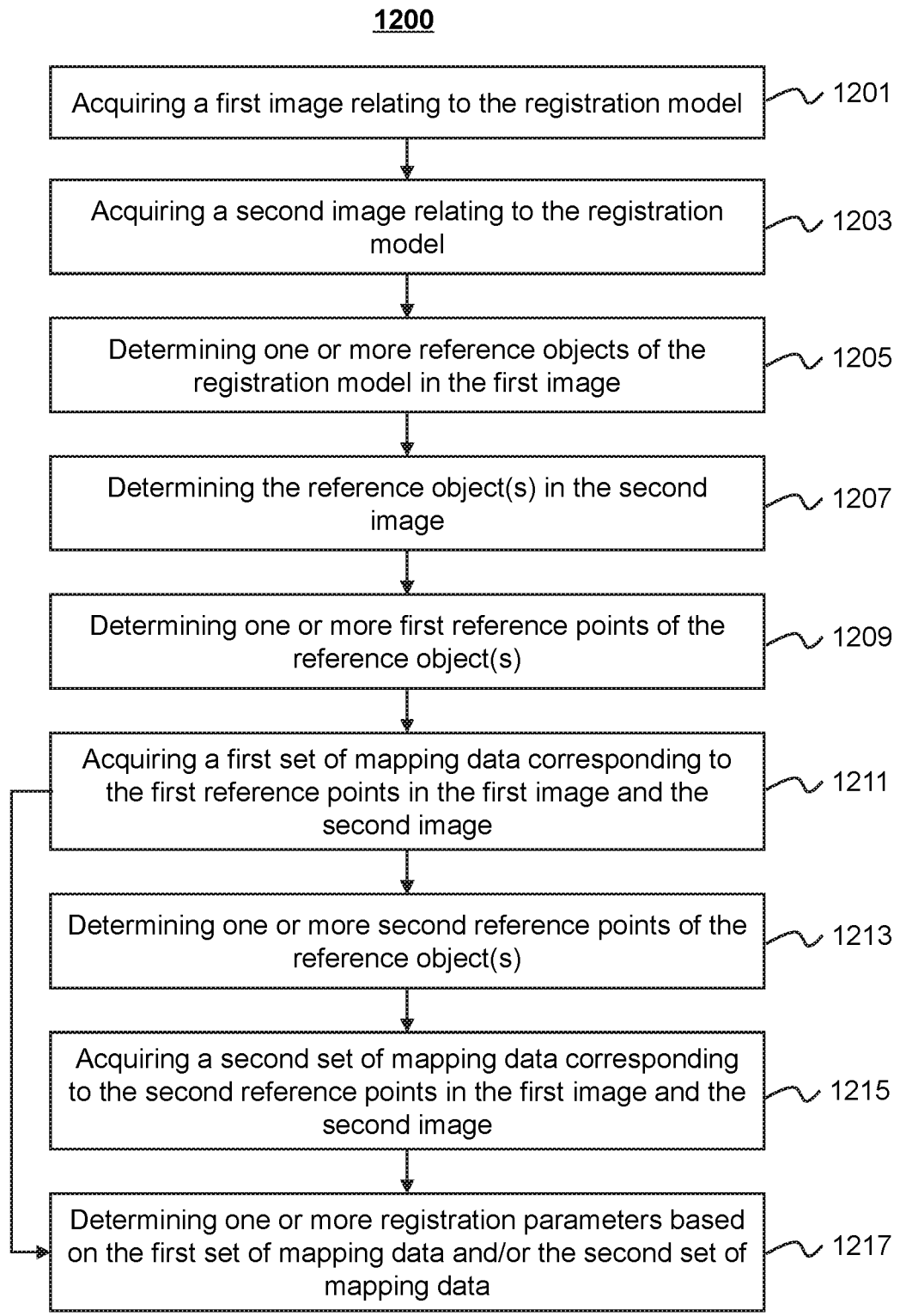
FIG. 12 is a flowchart illustrating another exemplary process for determining one or more registration parameters according to some embodiments of the present disclosure.

FIG. 12 is a flowchart illustrating an exemplary process for determining one or more registration parameters according to some embodiments of the present disclosure. In some embodiments, one or more operations of process 1200 illustrated in FIG. 12 for determining one or more registration parameters may be implemented in the imaging system 100 illustrated in FIG. 1. For example, the process 1200 illustrated in FIG. 12 may be stored in the storage device 130 in the form of instructions, and invoked and/or executed by the processing device 120 (e.g., the processor 210 of the computing device 200 as illustrated in FIG. 2, the CPU 340 of the mobile device 300 as illustrated in FIG. 3). As another example, a portion of the process 1200 may be implemented on the scanner 110. The operations of the illustrated process presented below are intended to be illustrative. In some embodiments, the process may be accomplished with one or more additional operations not described, and/or without one or more of the operations discussed. Additionally, the order in which the operations of the process as illustrated in FIG. 12 and described below is not intended to be limiting.

In 1201, a first image relating to a registration module (e.g., the registration model illustrated in FIG. 6) may be acquired. Operation 1201 may be performed by the first image acquisition unit 504. The first image may be a 3D image. Each voxel of the first image may have a three-dimensional coordinate position. In some embodiments, the registration model may be constructed before the first image is acquired. In some embodiments, the registration model may include one or more reference objects. In some embodiments, the reference object(s) may include two or more skew lines on different planes. More descriptions of the registration model may be found elsewhere in the present disclosure. See, for example, FIG. 6 and the description thereof. In some embodiments, the first image may include a CT image and/or an MR image. In some embodiments, the first image may be acquired from the scanner 110, the storage device 130, the terminal 140, and/or an external data source.

In 1203, a second image relating to the registration module may be acquired. Operation 1203 may be performed by the second image acquisition unit 506. The second image may be a 3D image. Each voxel of the second image may have a three-dimensional coordinate position. In some embodiments, the second image may include a PET image. It should be noted that the first image and the second image may be acquired sequentially or simultaneously. In some embodiments, the first image and the second image may be acquired in different single-modality imaging devices. In some embodiments, the first image and the second image may be acquired in a multi-modality imaging device. For example, a first portion of a multi-modality imaging device may acquire the first image (e.g., the CT image), and a second portion of the multi-modality imaging device may acquire the second image (e.g., the PET image).

In 1205, one or more reference objects of the registration model may be determined in the first image. Operation 1205 may be performed by the reference object determination unit 702. In some embodiments, the reference object(s) may include one or more skew lines on different planes. In some embodiments, a first location distribution of the reference object(s) in the first image may be determined. Merely by way of example, if the reference objects are skew lines on different planes, the first location distribution of the reference objects may be determined based on the slope of each skew line and a coordinate position of at least one point in each skew line in the first image. More descriptions of the process for determining the reference object(s) in the first image may be found elsewhere in the present disclosure. See, for example, FIG. 13 and the description thereof.

In 1207, the reference object(s) of the registration model may be determined in the second image. Operation 1207 may be performed by the reference object determination unit 702. In some embodiments, the reference object(s) may include one or more skew lines on different planes. In some embodiments, a second location distribution of the reference object(s) in the second image may be determined. Merely by way of example, if the reference objects are skew lines on different planes, the second location distribution of the reference objects may be determined based on the slope of each skew line and a coordinate position of at least one point in each skew line in the second image. More descriptions of the process for determining the reference object(s) in the second image may be found elsewhere in the present disclosure. See, for example, FIG. 14 and the description thereof.

In 1209, one or more first reference points of the reference object(s) may be determined. Operation 1209 may be performed by the reference point determination unit 704. In some embodiments, the reference objects may include one or more skew lines on different planes. In some embodiments, each of the skew lines may include one or more first reference points. In some embodiments, the positions of the first reference points may be determined based on a relative position of the reference objects. For example, the first reference points may be determined based on a shortest distance between every two reference objects. If there are N reference objects, then there may be $A_N^2$ first reference points. As illustrated in FIG. 11, line $L_1$ and line $L_2$ may be two skew lines on different planes. The first reference points, such as the first reference point $P_{10}$ on $L_1$ and the first reference point $P_{20}$ on $L_2$, may be determined based on the shortest distance between the two skew lines $L_1$ and $L_2$.

In 1211, a first set of mapping data corresponding to the first reference points in the first image and the second image may be acquired. Operation 1211 may be performed by the mapping data determination unit 706. The first set of mapping data corresponding to the first reference points may include information regarding a plurality of first coordinate positions of the first reference points in the first image and a plurality of second coordinate positions of the first reference points in the second image. The mapping data may reflect a mapping relation between the plurality of first coordinate positions of the first reference points in the first image and the plurality of second coordinate positions of the first reference points in the second image. For example, for the two first reference points $P_{10}$ and $P_{20}$ illustrated in FIG. 11, the first coordinate positions (e.g., $(X1_{P10}, Y1_{P10}, Z1_{P10})$ and $(X1_{P20}, Y1_{P20}, Z1_{P20})$) may be determined in the first image, and the second coordinate positions (e.g., $(X2_{P10}, Y2_{P10}, Z2_{P10})$ and $(X2_{P20}, Y2_{P20}, Z2_{P20})$) may be determined in the second image, respectively.

In 1213, one or more second reference points of the reference object(s) may be determined. Operation 1213 may be performed by the reference point determination unit 704. In some embodiments, the second reference point(s) may be determined based on one or more specific distances from the determined first reference points. For example, as illustrated in FIG. 11, the second reference points, such as $P_{11}$, $P_{11}'$, $P_{21}$, and $P_{21}'$, may be determined based on the first specific distance (e.g., $d_1$) from the corresponding first reference points $P_{10}$ and $P_{20}$. As another example, as illustrated in FIG. 11, the second reference points, such as $P_{12}$, $P_{12}'$, $P_{22}$, and $P_{22}'$, may be determined based on the second specific distance (e.g., $d_2$) from the corresponding first reference points $P_{10}$ and $P_{20}$.

In 1215, a second set of mapping data corresponding to the second reference points in the first image and the second image may be acquired. Operation 1215 may be performed by the mapping data determination unit 706. Similar to the first set of mapping data, the second set of mapping data corresponding to the second reference points may include information regarding a plurality of third coordinate positions of the second reference points in the first image and a plurality of fourth coordinate positions of the second reference points in the second image. The mapping data may reflect a mapping relation between the plurality of third coordinate positions of the second reference points in the first image and the plurality of fourth coordinate positions of the second reference points in the second image. For example, for the second reference points $P_{11}$ and $P_{21}$ illustrated in FIG. 11, the third coordinate positions (e.g., $(X3_{P11}, Y3_{P11}, Z3_{P11})$ and $(X3_{P21}, Y3_{P21}, Z3_{P21})$) may be determined in the first image, and the fourth coordinate positions (e.g., $(X4_{P11}, Y4_{P11}, Z4_{P11})$ and $(X4_{P21}, Y4_{P21}, Z4_{P21})$) may be determined in the second image, respectively.

In 1217, one or more registration parameters may be determined based on the first set of mapping data and/or the second set of mapping data. Operation 1217 may be performed by the registration parameter determination unit 708. In some embodiments, the registration parameters may include a rotation matrix and a translation vector. More descriptions of the registration parameters may be found elsewhere in the present disclosure. See, for example, FIG. 10 and the description thereof.

In some embodiments, an exemplary relationship between the mapping data (e.g., the first set of mapping data and/or the second set of mapping data) and the registration parameters may be described as Equation (1):

$$SI = R \times FI + T, \quad (1)$$

where SI may be the corresponding coordinate positions of the reference points (e.g., the first reference points and/or the second reference points) in the second image, FI may be the coordinate positions of the same reference positions in the first image, R may be the rotation matrix, and T may be the translation vector. Specifically, Equation (1) may be expressed in a form of matrix, as illustrated in Equation (2):

$$\begin{bmatrix} X_{SI} \\ Y_{SI} \\ Z_{SI} \end{bmatrix} = \begin{bmatrix} r_1 & r_2 & r_3 \\ r_4 & r_5 & r_6 \\ r_7 & r_8 & r_9 \end{bmatrix} \begin{bmatrix} X_{FI} \\ Y_{FI} \\ Z_{FI} \end{bmatrix} + \begin{bmatrix} T_x \\ T_y \\ T_z \end{bmatrix}, \quad (2)$$

where ($X_{SI}$, $Y_{SI}$, $Z_{SI}$) may be the corresponding coordinate positions of the reference points (e.g., the first reference points and/or the second reference points) in the second image, ($X_{FI}$, $Y_{FI}$, $Z_{FI}$) may be the coordinate positions of the same reference points in the first image, $$\begin{bmatrix} r_1 & r_2 & r_3 \\ r_4 & r_5 & r_6 \\ r_7 & r_8 & r_9 \end{bmatrix}$$

may be the rotation matrix, and $$\begin{bmatrix} T_x \\ T_y \\ T_z \end{bmatrix}$$

may be the translation vector. Each element of the rotation matrix may relate to one or more Euler angles of the rotation of the X axis, Y axis, and/or Z axis of the reference points for image registration. $T_x$, $T_y$, and $T_z$ may refer to the translation parameter relating to translation of the reference points in the X axis direction, the Y axis direction, and the Z axis direction, respectively.

More particularly, in some embodiments, Equation (2) may be further transformed to Equation (3), as illustrated below:

$$\begin{bmatrix} X_{SI} \\ Y_{SI} \\ Z_{SI} \\ 1 \end{bmatrix} = \begin{bmatrix} r_1 & r_2 & r_3 & T_x \\ r_4 & r_5 & r_6 & T_y \\ r_7 & r_8 & r_9 & T_z \\ 0 & 0 & 0 & 1 \end{bmatrix} \begin{bmatrix} X_{FI} \\ Y_{FI} \\ Z_{FI} \\ 1 \end{bmatrix}, \quad (3)$$

where $$\begin{bmatrix} r_1 & r_2 & r_3 & T_x \\ r_4 & r_5 & r_6 & T_y \\ r_7 & r_8 & r_9 & T_z \\ 0 & 0 & 0 & 1 \end{bmatrix}$$

may refer to the registration parameters M associated with the mapping data (e.g., the first set of mapping data and/or the second set of mapping data). Exemplary algorithms for determining registration parameters may include a random sample consensus (RANSAC) algorithm, an iterative closest point (ICP) algorithm, a residual histogram analysis (RHA) algorithm, a J-Linkage algorithm, a kernel fitting algorithm, a gradient-based algorithm, a fast decent algorithm, etc.

It should be noted that for persons having ordinary skills in the art, the number of reference points is not intended to limit the scope of the present disclosure. The number of reference points may satisfy a solution condition for Equation (3) (or Equation (2)). In some embodiments, according to the solution condition of Equation (3), the registration parameters M may be determined based on the mapping data including at least four reference points. For example, at least four reference points (e.g., $P_{10}$, $P_{20}$, $P_{11}$, $P_{21}$ as illustrated in FIG. 11) may be determined in operations 1209 and/or 1213 to obtain a solution of Equation (3). In some embodiments, the reference objects of the registration model may include at least three skew lines on different planes, and thus, in 1217, the registration parameter determination unit 708 may directly determine the registration parameters based on the first set of mapping data acquired in 1211 corresponding to the first reference points (e.g., six first reference points determined based on the three skew lines). That is, after operation 1211 is performed, process 1200 may proceed to 1217, and operations 1213 and 1215 may be omitted. It should be understood that with larger number of reference points, the accuracy of the determined registration parameters may be higher.

It should be noted that the description of the process 1200 is provided for the purposes of illustration, and not intended to limit the scope of the present disclosure. For persons having ordinary skills in the art, various variations and modifications may be conducted under the teaching of the present disclosure. However, those variations and modifications do not depart from the scope of the present disclosure. For example, operation 1201 and operation 1203 may be integrated into one single operation. As another example, operation 1205 and operation 1207 may be integrated into one single operation. As a further example, operation 1213 may be performed before operation 1211. As still a further example, operation 1215 may be performed before operation 1213. As still a further example, operation 1209 and 1213 may be integrated into one single operation. As still a further example, operation 1211 and operation 1215 may be integrated into one single operation.

Figure 13:
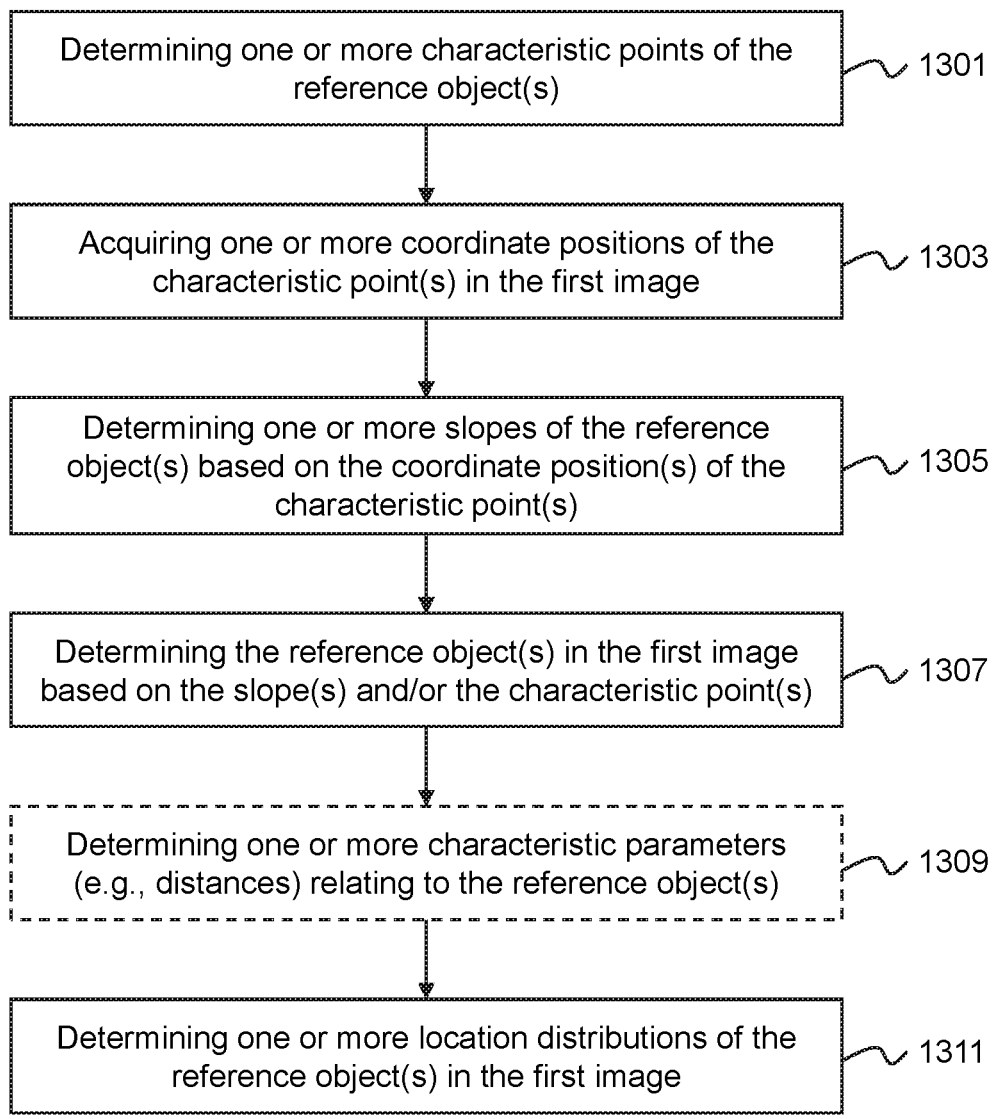
FIG. 13 is a flowchart illustrating an exemplary process for determining location distribution of one or more reference objects in a first image according to some embodiments of the present disclosure.

FIG. 13 is a flowchart illustrating an exemplary process 1300 for determining location distribution of one or more reference objects in a first image according to some embodiments of the present disclosure. In some embodiments, one or more operations of process 1300 illustrated in FIG. 13 for determining location distribution of one or more reference objects may be implemented in the imaging system 100 illustrated in FIG. 1. For example, the process 1300 illustrated in FIG. 13 may be stored in the storage device 130 in the form of instructions, and invoked and/or executed by the processing device 120 (e.g., the processor 210 of the computing device 200 as illustrated in FIG. 2, the CPU 340 of the mobile device 300 as illustrated in FIG. 3). As another example, a portion of the process 1300 may be implemented on the scanner 110. In some embodiments, operation 1205 illustrated in FIG. 12 may be performed according to the process 1300. The operations of the illustrated process presented below are intended to be illustrative. In some embodiments, the process may be accomplished with one or more additional operations not described, and/or without one or more of the operations discussed. Additionally, the order in which the operations of the process as illustrated in FIG. 13 and described below is not intended to be limiting.

In 1301, one or more characteristic points of the reference object(s) may be determined. Operation 1301 may be performed by the characteristic point determination subunit 802. A characteristic point may refer to a point at a characteristic position in a reference object. In some embodiments, a characteristic position may refer to an intersection position of a reference object and an auxiliary plane or auxiliary line. A reference object may include one or more characteristic points. Two or more characteristic points of the reference object(s) may be in a same plane. In some embodiments, the reference object(s) may include at least two skew lines on different planes. In some embodiments, one or more intersection points between two or more (e.g., three) parallel planes and the reference object(s) may be determined. In some embodiments, the intersection points may be designated as the characteristic points. In some embodiments, the parallel planes may be parallel to a coronal plane, a sagittal plane, a transverse plane, or a plane having any oblique angle in a spatial coordinate system.

In some embodiments, the first image may be a 3D image. A cross plane of the 3D image may be formed at each plane of the parallel planes. Accordingly, a two-dimensional image may be obtained at the cross plane. Each reference object may have a characteristic point in the two-dimensional image. Thus, a plurality of characteristic points may be determined based on a plurality of two-dimensional images corresponding to the parallel planes. It should be noted that in some embodiments, a characteristic point of a reference object may be represented by a region of pixels/voxels in a two-dimensional image, and a central pixel/voxel or any pixel/voxel of the region may be designated as the characteristic point. If the reference objects include at least two skew lines on different planes, and the number of the parallel planes is three, then at least six characteristic points may be determined in 1301. It should be understood for persons having ordinary skills in the art, the number of the characteristic points is not intended to be limiting. In some embodiments, the number of the characteristic points may be varied. All such variations are within the protection scope of the present disclosure.

In 1303, one or more coordinate positions of the characteristic point(s) in the first image may be acquired. Operation 1303 may be performed by the characteristic point determination subunit 802. In some embodiments, the first image may include a CT image and/or an MR image. As the reference objects are constructed with specific materials, a point of the reference objects may correspond to a pixel/voxel of the first image that has a specific image value (e.g., a gray level, brightness, etc.). In some embodiments, in the first image, the image values corresponding to the characteristic points may be different from that corresponding to other points excluding the reference objects (e.g., a background). In some embodiments, the characteristic points may be extracted from the plurality of two-dimensional images corresponding to the parallel planes. In some embodiments, the characteristic points may be extracted based on one or more segmentation algorithms. Exemplary segmentation algorithms may include a threshold segmentation algorithm, a region growing segmentation algorithm, an energy-based 3D reconstruction segmentation algorithm, a level set-based segmentation algorithm, a region split and/or merge segmentation algorithm, an edge tracking segmentation algorithm, a statistical pattern recognition algorithm, a C-means clustering segmentation algorithm, a deformable model segmentation algorithm, a graph search segmentation algorithm, a neural network segmentation algorithm, a geodesic minimal path segmentation algorithm, a target tracking segmentation algorithm, an atlas-based segmentation algorithm, a rule-based segmentation algorithm, a coupled surface segmentation algorithm, a model-based segmentation algorithm, a deformable organism segmentation algorithm, a model matching algorithm, an artificial intelligence algorithm, or the like, or any combination thereof. Merely by way of example, the characteristic points may be extracted based on a threshold relating to an image-related value (e.g., a gray level). The threshold may be a default value determined by the imaging system 100, or may be preset by a user or operator via the terminal(s) 140. Therefore, the coordinate positions of the extracted characteristic points may be acquired accordingly.

Merely by way of example, if the reference objects include two skew lines on different planes (as shown in FIG. 6 and FIG. 11), and the number of the parallel planes is three, then at least six characteristic points may be determined, and six coordinate positions may be acquired. The three parallel planes may include a first plane, a second plane, and a third plane. A characteristic point $Q_1$ may be determined based on the first plane and a first reference object. A characteristic point $Q_2$ may be determined based on the first plane and a second reference object. Similarly, a characteristic points $Q_3$ may be determined based on the second plane and the first reference object. A characteristic point $Q_4$ may be determined based on the second plane and the second reference object. A characteristic point $Q_5$ may be determined based on the third plane and the first reference object. A characteristic point $Q_6$ may be determined based on the third plane and the second reference object. Furthermore, the corresponding coordinate positions of the characteristic points, such as $Q_1$, $Q_2$, $Q_3$, $Q_4$, $Q_5$, and $Q_6$, may be acquired. In some embodiments, the characteristic point determination subunit 802 may send data relating to the acquired coordinate positions to the slope determination subunit 804 for further processing.

In 1305, one or more slopes of the reference object(s) may be determined based on the coordinate position(s) of the characteristic point(s). Operation 1305 may be performed by the slope determination subunit 804. It should be understood that two points may define a straight line. Thus, every two characteristic points may define a straight line, and a slope of the straight line may be determined based on the coordinate positions of the every two characteristic points. Accordingly, a first set of slopes may be determined based on the characteristic points. If there are N (N may be an integer larger than 1) characteristic points, $C_N^2$ slopes may be determined in the first set of slopes. The first set of slopes may include a first subset of slopes and a second subset of slopes. The first subset of slopes may be determined based on every two characteristic points that belong to a same reference object. The second subset of slopes may be determined based on every two characteristic points that belong to different reference objects. The first subset of slopes may be regarded as real slopes corresponding to the reference objects, while the second subset of slopes may be regarded as noise data. The slopes determined based on two or more characteristic points that belong to a same reference object may be the same, while the slopes determined based on two or more characteristic points that belong to different reference objects may be different. Thus, the first subset of slopes may be distinguished from the second subset of slopes.

In some embodiments, the first set of slopes may be divided into a plurality of groups based on the values of the first set of slopes. One or more slopes in each group may be substantially the same. One or more target groups that have a maximum number of slopes may be determined. Then the values of the target groups may be designated as the slopes corresponding to the reference objects.

Merely by way of example, if there are six characteristic points including $Q_1$, $Q_2$, $Q_3$, $Q_4$, $Q_5$, and $Q_6$ as described above, $C_6^2$ (i.e., 15) slopes may be determined in 1305. The first set of slopes may include 15 slopes represented by ($Q_1$, $Q_2$), ($Q_1$, $Q_3$), ($Q_1$, $Q_4$), ($Q_1$, $Q_5$), ($Q_1$, $Q_6$), ($Q_2$, $Q_3$), ($Q_2$, $Q_4$), ($Q_2$, $Q_5$), ($Q_2$, $Q_6$), ($Q_3$, $Q_4$), ($Q_3$, $Q_5$), ($Q_3$, $Q_6$), ($Q_4$, $Q_5$), ($Q_4$, $Q_6$), and ($Q_5$, $Q_6$). The characteristic points $Q_1$, $Q_3$, and Q belong to the first reference object, therefore, the values of slopes ($Q_1$, $Q_3$), ($Q_1$, $Q_5$), and ($Q_3$, $Q_5$) may be the same. Accordingly, as the characteristic points $Q_2$, $Q_4$ and $Q_6$ belong to the second reference object, the values of slopes ($Q_2$, $Q_4$), ($Q_2$, $Q_6$), and ($Q_4$, $Q_6$) may be the same. The first set of slopes may be divided into at least two groups based on the values of the first set of slopes. In some embodiments, the slopes having the same values may belong to a same group. For example, the slopes ($Q_1$, $Q_3$), ($Q_1$, $Q_5$), and ($Q_3$, $Q_5$) may belong to a first group, and the slopes ($Q_2$, $Q_4$), ($Q_2$, $Q_6$), and ($Q_4$, $Q_6$) may belong to a second group. That is, the first group may have 3 slopes, and the second group may have 3 slopes. The values of residual nine slopes may be different from each other, each of the nine slopes may belong to a single group. Then the value(s) of the group(s) having a maximum number of slopes may be designated as the slope(s) of the reference object(s). For example, the value of the first group may be designated as the slope of the first reference object (also referred to herein as a first slope), and the value of the second group may be designated as the slope of the second reference object (also referred to herein as a second slope).

In 1307, the reference object(s) in the first image may be determined based on the slope(s) and/or the characteristic point(s). Operation 1307 may be performed by the location determination subunit 808. In some embodiments, if a reference object is a skew line, the reference object may be determined based on a point (e.g., a characteristic point or reference point in the reference object) and a slope. In some embodiments, if a reference object is a skew line, the reference object may be determined based on two points (e.g., two characteristic points or reference points in the reference object). For example, the first reference object may be determined based on the coordinate positions of two of the characteristic points (e.g., $Q_1$ and $Q_3$) and/or the first slope. Similarly, the second reference object may be determined based on the coordinate positions of two of the characteristic points (e.g., $Q_2$ and $Q_4$) and/or the second slope.

In 1309, one or more characteristic parameters (e.g., distances) relating to the reference object(s) may be determined. Operation 1311 may be performed by the characteristic parameter determination subunit 806. A characteristic parameter relating to the reference object(s) may be a parameter that may be used to determine a relative position of the reference object(s). In some embodiments, a characteristic parameter may be a distance (e.g., a shortest distance) between every two reference objects. In some embodiments, a common vertical line of every two reference objects may have two intersection points with the every two reference objects, and the distance between the two intersection points may represent a characteristic parameter relating to the every two reference objects.

In 1311, one or more location distributions of the reference object(s) in the first image may be determined. Operation 1311 may be performed by the location determination subunit 808. In some embodiments, the location distribution(s) of the reference object(s) may be determined based on the reference object(s) determined in 1307 and/or the characteristic parameter(s) determined in 1309. For example, a location distribution of the first reference object in the first image may be determined based on the coordinate positions of two of the characteristic points (e.g., $Q_1$ and $Q_3$) and/or the first slope, and then a location distribution of the second reference object in the first image may be determined based on the location distribution of the first reference object and a shortest distance between the first reference object and the second reference object. In some embodiments, the location distribution(s) of the reference object(s) in the first image may be determined as described in connection with operation 1307, and the determined location distribution(s) may be adjusted or corrected based on the characteristic parameter(s) determined in 1309.

It should be noted that the description of the process 1300 is provided for the purposes of illustration, and not intended to limit the scope of the present disclosure. For persons having ordinary skills in the art, various variations and modifications may be conducted under the teaching of the present disclosure. However, those variations and modifications do not depart from the scope of the present disclosure. For example, operation 1301 and operation 1303 may be integrated into one single operation. As another example, operations 1307, 1309, and/or 1311 may be integrated into one single operation. As a further example, operation 1309 and/or operation 1311 may be omitted.

Figure 14:
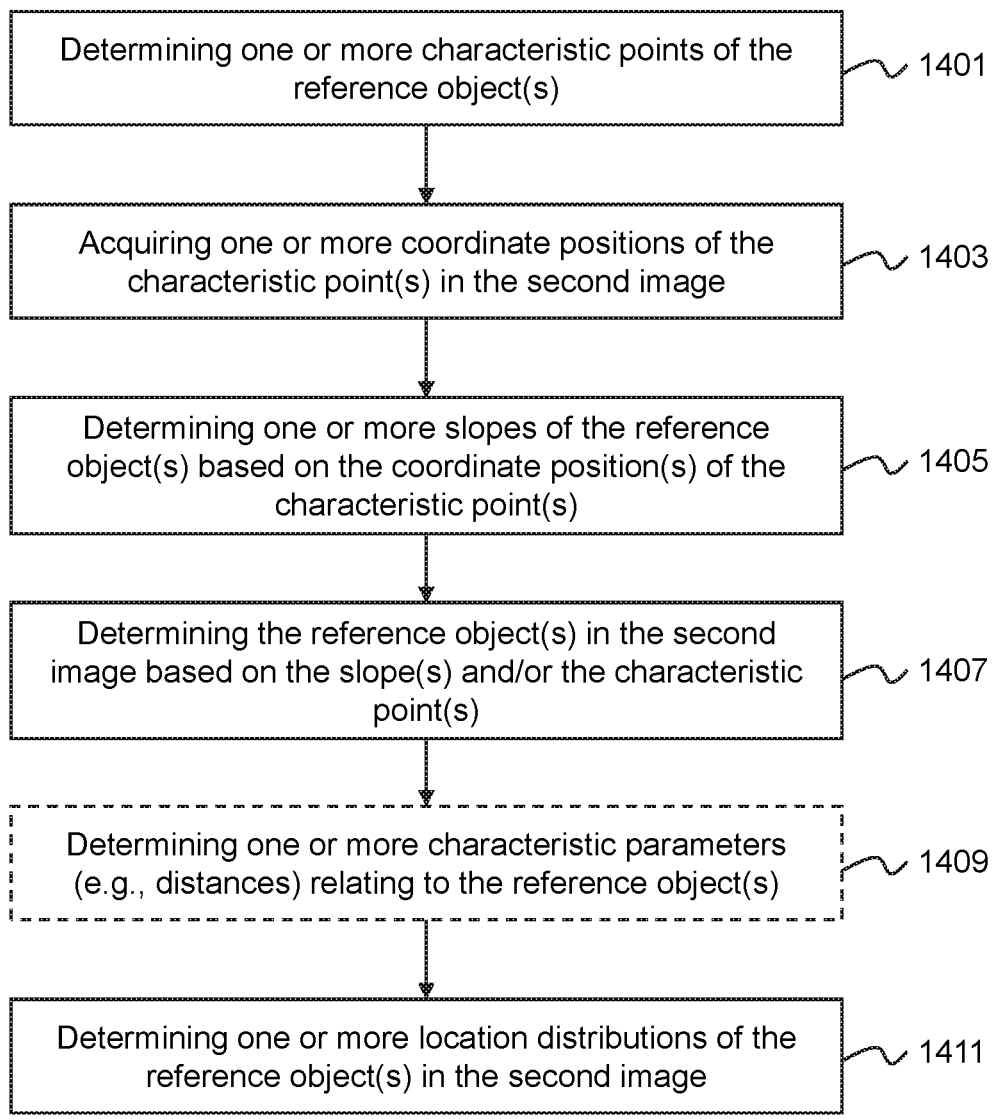
FIG. 14 is a flowchart illustrating an exemplary process for determining location distributions of one or more reference objects in a second image according to some embodiments of the present disclosure.

FIG. 14 is a flowchart illustrating an exemplary process 1400 for determining location distribution of one or more reference objects in a second image according to some embodiments of the present disclosure. In some embodiments, the location distribution of one or more reference objects in the second image may be determined similarly to process 1300. In some embodiments, one or more operations of process 1400 illustrated in FIG. 14 for determining location distribution of one or more reference objects may be implemented in the imaging system 100 illustrated in FIG. 1. For example, the process 1400 illustrated in FIG. 14 may be stored in the storage device 130 in the form of instructions, and invoked and/or executed by the processing device 120 (e.g., the processor 210 of the computing device 200 as illustrated in FIG. 2, the CPU 340 of the mobile device 300 as illustrated in FIG. 3). As another example, a portion of the process 1400 may be implemented on the scanner 110. In some embodiments, operation 1207 illustrated in FIG. 12 may be performed according to the process 1400. The operations of the illustrated process presented below are intended to be illustrative. In some embodiments, the process may be accomplished with one or more additional operations not described, and/or without one or more of the operations discussed. Additionally, the order in which the operations of the process as illustrated in FIG. 14 and described below is not intended to be limiting.

In 1401, one or more characteristic points of the reference object(s) may be determined. Operation 1401 may be performed by the characteristic point determination subunit 802. A characteristic point may refer to a point at a characteristic position in a reference object. In some embodiments, a characteristic position may refer to an intersection position of a reference object and an auxiliary plane or auxiliary line. A reference object may include one or more characteristic points. Two or more characteristic points of the reference object(s) may be in a same plane. In some embodiments, the reference object(s) may include at least two skew lines on different planes. In some embodiments, one or more intersect points between two or more (e.g., three) parallel planes and the reference object(s) may be determined. In some embodiments, the intersection points may be designated as the characteristic points. In some embodiments, the parallel planes may be parallel to a coronal plane, a sagittal plane, a transverse plane, or a plane having any oblique angle in a spatial coordinate system.

In some embodiments, the second image may be a 3D image. A cross plane of the 3D image may be formed at each plane of the parallel planes. Accordingly, a two-dimensional image may be obtained at the cross plane. Each reference object may have a characteristic point in the two-dimensional image. One or more characteristic points may be determined in the two-dimensional image. Thus, a plurality of characteristic points may be determined based on a plurality of two-dimensional images corresponding to the parallel planes. It should be noted that in some embodiments, a characteristic point of a reference object may be represented by a region of pixels/voxels in a two-dimensional image, and a central pixel/voxel or any pixel/voxel of the region may be designated as the characteristic point. If the reference objects include at least two skew lines on different planes, and the number of the parallel planes is three, then at least six characteristic points may be determined in 1401. It should be understood for persons having ordinary skills in the art, the number of the characteristic points is not intended to be limiting. In some embodiments, the number of the characteristic points may be varied. All such variations are within the protection scope of the present disclosure.

In 1403, one or more coordinate positions of the characteristic point(s) in the second image may be acquired. Operation 1403 may be performed by the characteristic point determination subunit 802. In some embodiments, the second image may include a CT image and/or an MR image. As the reference objects are constructed with specific materials, a point of the reference objects may correspond to a pixel/voxel of the second image that has a specific image value (e.g., a gray level, brightness, etc.). In some embodiments, in the second image, the image values corresponding to the characteristic points may be different from that corresponding to other points excluding the reference objects (e.g., a background). In some embodiments, the characteristic points may be extracted from the plurality of two-dimensional images corresponding to the parallel planes. In some embodiments, the characteristic points may be extracted based on one or more segmentation algorithms described in FIG. 13. Merely by way of example, the characteristic points may be extracted based on a threshold relating to an image-related value (e.g., a gray level). The threshold may be a default value determined by the imaging system 100, or may be preset by a user or operator via the terminal(s) 140. Therefore, the coordinate positions of the extracted characteristic points may be acquired accordingly.

Merely by way of example, if the reference objects include two skew lines on different planes (as shown in FIG. 6 and FIG. 11), and the number of the parallel planes is three, then at least six characteristic points may be determined, and six coordinate positions may be acquired. The three parallel planes may include a first plane, a second plane, and a third plane. A characteristic point $Q_1$ may be determined based on the first plane and a first reference object. A characteristic point $Q_2$ may be determined based on the first plane and a second reference object. Similarly, a characteristic points $Q_3$ may be determined based on the second plane and the first reference object. A characteristic point $Q_4$ may be determined based on the second plane and the second reference object. A characteristic point $Q_5$ may be determined based on the third plane and the first reference object. A characteristic point $Q_6$ may be determined based on the third plane and the second reference object. Furthermore, the corresponding coordinate positions of the characteristic points, such as $Q_1$, $Q_2$, $Q_3$, $Q_4$, $Q_5$, and $Q_6$, may be acquired. In some embodiments, the characteristic point determination subunit 802 may send data relating to the acquired coordinate positions to the slope determination subunit 804 for further processing.

In 1405, one or more slopes of the reference object(s) may be determined based on the coordinate position(s) of the characteristic point(s). Operation 1405 may be performed by the slope determination subunit 804. It should be understood that two points may define a straight line. Thus, every two characteristic points may define a straight line, and a slope of the straight line may be determined based on the coordinate positions of the every two characteristic points. Accordingly, a second set of slopes may be determined based on the characteristic points. If there are N (N may be an integer larger than 1) characteristic points, $C_N^2$ slopes may be determined in the second set of slopes. The second set of slopes may include a third subset of slopes and a fourth subset of slopes. The third subset of slopes may be determined based on every two characteristic points that belong to a same reference object. The fourth subset of slopes may be determined based on every two characteristic points that belong to different reference objects. The third subset of slopes may be regarded as real slopes corresponding to the reference objects, while the fourth subset of slopes may be regarded as noise data. The slopes determined based on two or more characteristic points that belong to a same reference object may be the same, while the slopes determined based on two or more characteristic points that belong to different reference objects may be different. Thus, the third subset of slopes may be distinguished from the fourth subset of slopes.

In some embodiments, the second set of slopes may be divided into a plurality of groups based on values of the second set of slopes. One or more slopes in each group may be substantially the same. One or more target groups that have a maximum number of slopes may be determined. Then the values of the target groups may be designated as the slopes corresponding to the reference objects.

Merely by way of example, if there are six characteristic points including $Q_1$, $Q_2$, $Q_3$, $Q_4$, $Q_5$, and $Q_6$ as described above, $C_6^2$ (i.e., 15) slopes may be determined in 1405. The second set of slopes may include 15 slopes represented by $(Q_1, Q_2)$, $(Q_1, Q_3)$, $(Q_1, Q_4)$, $(Q_1, Q_5)$, $(Q_1, Q_6)$, $(Q_2, Q_3)$, $(Q_2, Q_4)$, $(Q_2, Q_5)$, $(Q_2, Q_6)$, $(Q_3, Q_4)$, $(Q_3, Q_5)$, $(Q_3, Q_6)$, $(Q_4, Q_5)$, $(Q_4, Q_6)$, and $(Q_5, Q_6)$. The characteristic points $Q_1$, $Q_3$, and Q belong to the first reference object, therefore, the values of slopes $(Q_1, Q_3)$, $(Q_1, Q_5)$, and $(Q_3, Q_5)$ may be the same. Accordingly, as the characteristic points $Q_2$, $Q_4$ and $Q_6$ belong to the second reference object, the values of slopes $(Q_2, Q_4)$, $(Q_2, Q_6)$, and $(Q_4, Q_6)$ may be the same. The second set of slopes may be divided into at least two groups based on the values of the second set of slopes. In some embodiments, the slopes having the same values may belong to a same group. For example, the slopes $(Q_1, Q_3)$, $(Q_1, Q_5)$, and $(Q_3, Q_5)$ may belong to a third group, and the slopes $(Q_2, Q_4)$, $(Q_2, Q_6)$, and $(Q_4, Q_6)$ may belong to a fourth group. That is, the third group may have 3 slopes, and the fourth group may have 3 slopes. The values of residual nine slopes may be different from each other, each of the nine slopes may belong to a single group. Then the value(s) of the group(s) having a maximum number of slopes may be designated as the slope(s) of the reference object(s). For example, the value of the third group may be designated as the slope of the first reference object (also referred to herein as a first slope), and the value of the fourth group may be designated as the slope of the second reference object (also referred to herein as a second slope).

In 1407, the reference object(s) in the second image may be determined based on the slope(s) and/or the characteristic point(s). Operation 1407 may be performed by the location determination subunit 808. In some embodiments, if a reference object is a skew line, the reference object may be determined based on a point (e.g., a characteristic point in the reference object) and a slope. In some embodiments, if a reference object is a skew line, the reference object may be determined based on two points (e.g., two characteristic points in the reference object). For example, the first reference object may be determined based on the coordinate positions of two of the characteristic points (e.g., $Q_1$, $Q_3$, $Q_5$)

and/or the first slope. Similarly, the second reference object may be determined based on the coordinate positions of two of the characteristic points (e.g., $Q_2$, $Q_4$, $Q_6$) and the second slope.

In 1409, one or more characteristic parameters (e.g., distances) relating to the reference object(s) may be determined. Operation 1411 may be performed by the characteristic parameter determination subunit 806. A characteristic parameter relating to the reference object(s) may be a parameter that may be used to determine a relative position of the reference object(s). In some embodiments, a characteristic parameter may be a distance (e.g., a shortest distance) between every two reference objects. In some embodiments, a common vertical line of every two reference objects may have two intersection points with the every two reference objects, and the distance between the two intersection points may represent a characteristic parameter relating to the every two reference objects.

In 1411, one or more location distributions of the reference object(s) in the second image may be determined. Operation 1411 may be performed by the location determination subunit 808. In some embodiments, the location distribution(s) of the reference object(s) may be determined based on the reference object(s) determined in 1407 and/or the characteristic parameter(s) determined in 1409. For example, a location distribution of the first reference object in the second image may be determined based on the coordinate positions of two of the characteristic points (e.g., $Q_1$, $Q_3$, $Q_5$) and/or the first slope, and then a location distribution of the second reference object in the second image may be determined based on the location distribution of the first reference object and a shortest distance between the first reference object and the second reference object. In some embodiments, the location distribution(s) of the reference object(s) in the second image may be determined as described in connection with operation 1407, and the determined location distribution(s) may be adjusted or corrected based on the characteristic parameter(s) determined in 1409.

It should be noted that the description of the process 1400 is provided for the purposes of illustration, and not intended to limit the scope of the present disclosure. For persons having ordinary skills in the art, various variations and modifications may be conducted under the teaching of the present disclosure. However, those variations and modifications do not depart from the scope of the present disclosure. For example, operation 1401 and operation 1403 may be integrated into one single operation. As another example, operations 1407, 1409, and/or 1411 may be integrated into one single operation. As a further example, operation 1409 and/or operation 1411 may be omitted. As still a further example, if process 1300 is performed before process 1400, then operation 1401 may be omitted.

Figure 15:
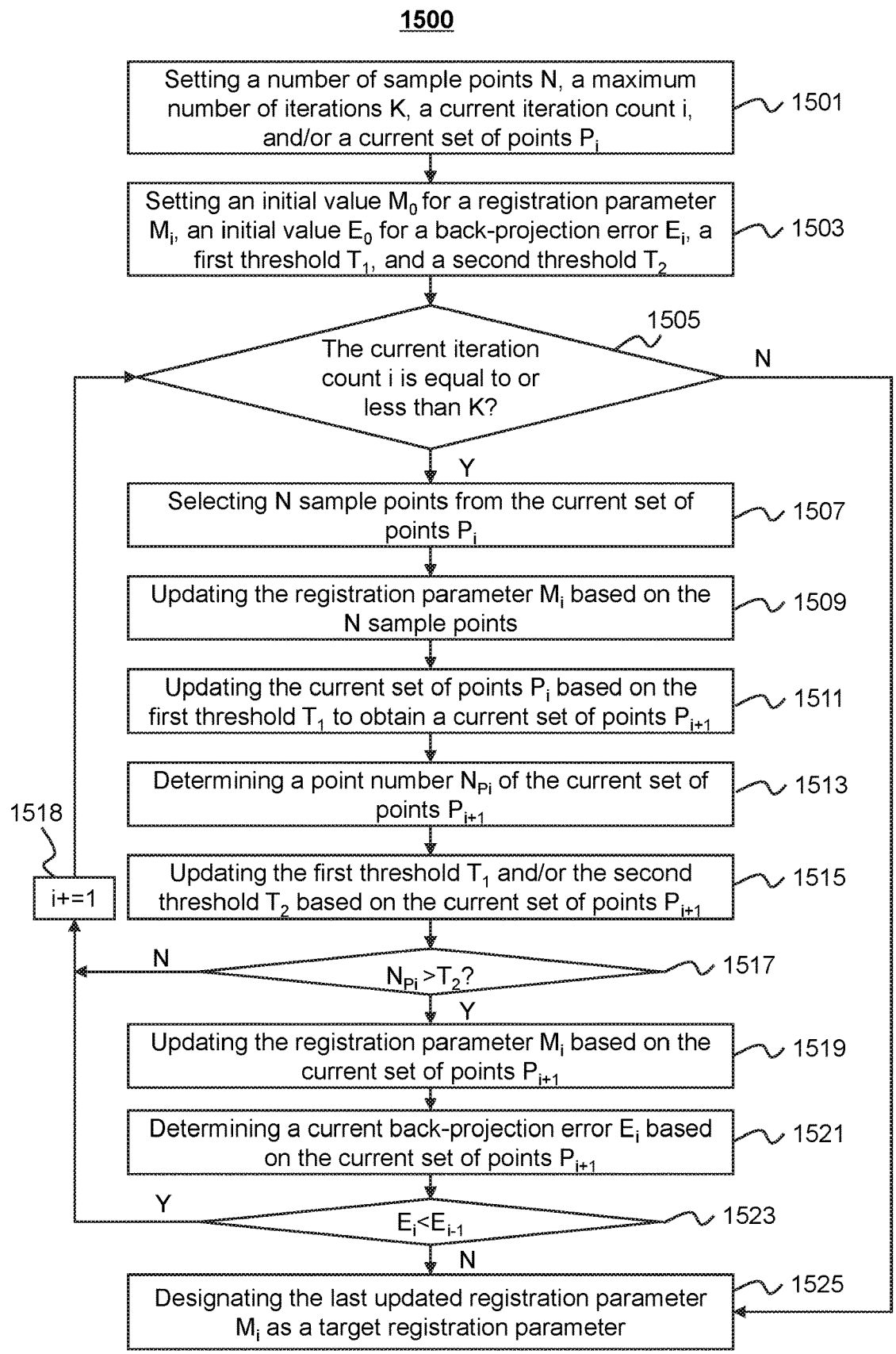
FIG. 15 is flowchart illustrating an exemplary process for determining one or more registration parameters according to some embodiments of the present disclosure.

FIG. 15 is a flowchart illustrating an exemplary process 1500 for determining one or more registration parameters according to some embodiments of the present disclosure. In some embodiments, one or more operations of process 1500 illustrated in FIG. 15 for determining registration parameters may be implemented in the imaging system 100 illustrated in FIG. 1. For example, the process 1500 illustrated in FIG. 15 may be stored in the storage device 130 in the form of instructions, and invoked and/or executed by the processing device 120 (e.g., the processor 210 of the computing device 200 as illustrated in FIG. 2, the CPU 340 of the mobile device 300 as illustrated in FIG. 3). As another example, a portion of the process 1500 may be implemented on the scanner 110. In some embodiments, operation 1217 illustrated in FIG. 12 may be performed according to the process 1500. In some embodiments, process 1500 may be performed by the registration parameter determination unit 708. The operations of the illustrated process presented below are intended to be illustrative. In some embodiments, the process may be accomplished with one or more additional operations not described, and/or without one or more of the operations discussed. Additionally, the order in which the operations of the process as illustrated in FIG. 15 and described below is not intended to be limiting.

In some embodiments, the registration parameter(s) may be determined based on a plurality of iterations. In some embodiments, the plurality of iterations may be performed based on a random sample consensus (RANSAC) algorithm. The process 1500 for determining registration parameters may be performed according to the RANSAC algorithm.

In 1501, one or more parameters may be set. The parameters may include a number of sample points N, a maximum number of iterations K, a current iteration count i, and/or a current set of points $P_i$. Operation 1501 may be performed by the parameter setting subunit 902. In some embodiments, the sample points may be sampled from the reference points of the reference objects. The reference points may include the first reference points, the second reference points, or the like, or any combination thereof. In some embodiments, the number of sample points N may refer to a minimum number of sample points for determining the registration parameters. N may be an integer equal to or greater than 3, such as 4, 5, 6, etc. The maximum number of iterations K may be an integer larger than 1, for example, 50, 100, 1000, etc. A current iteration count i may be an integer larger than 0. In some embodiments, the parameters illustrated above may be default values determined by the imaging system 100, or may be preset by a user or operator via the terminal(s) 140. For example, the current iteration count i may be preset as 1. In some embodiments, if the current iteration count i is 1, the current set of points $P_1$ may include the set of reference points determined in 1003, 1209, or 1213. For example, the current set of points $P_1$ may include all or a portion of the first reference points determined in 1209 and/or all or a portion of the second reference points determined in 1213.

In 1503, an initial value $M_0$ for a registration parameter $M_i$, an initial value $E_0$ for a back-projection error $E_i$, a first threshold $T_1$, and a second threshold $T_2$ may be set. Operation 1503 may be performed by the parameter setting subunit 902. In some embodiments, the first threshold $T_1$ may refer to a median value of registration errors of all the reference points in the current set of points $P_i$. The registration errors may relate to the differences between the coordinate positions of all the reference points in the current set of points $P_i$ before and after registration using the registration parameter $M_i$. In some embodiments, the second threshold $T_2$ may refer to an integer equal to or less than a half of the number of the reference points in the current set of points $P_i$. In some embodiments, the first threshold $T_1$ and/or the second threshold $T_2$ may be default value(s) determined by the imaging system 100, or may be preset by a user or operator via the terminal(s) 140.

In some embodiments, the initial value $M_0$ may be determined based on Equation (3) and the mapping data relating to all the reference points in the current set of points $P_1$. For example, the initial value $M_0$ may be a solution of Equation (3) when mapping data relating to the current set of points $P_1$ is brought into Equation (3).

In some embodiments, the back-projection error $E_i$ may relate to the registration errors of one or more reference points in the current set of points $P_i$. In some embodiments, the back-projection error $E_i$ may be a mean square error (MSE) of the registration errors. Merely by way of example, if the coordinate position of a point A in the first image is $(X_{FIA}, Y_{FIA}, Z_{FIA})$, and the coordinate position of the point A in the second image is $(X_{SIA}, Y_{SIA}, Z_{SIA})$, a registered coordinate position of the point A may be determined as $(X_A, Y_A, Z_A)$ after registration using the registration parameter $M_i$. The difference between the coordinate position of the point A in the second image (e.g., $(X_{SIA}, Y_{SIA}, Z_{SIA})$) and the registered coordinate position of the point A (e.g., $(X_A, Y_A, Z_A)$) may be regarded as a registration error. If there are L points in the current set of points $P_i$, there may be L registration errors, and the back-projection error $E_i$ may be a mean square error (MSE) of the L registration errors. In some embodiments, the initial value $E_0$ of the back-projection error $E_i$ may be determined based on the initial registration parameter $M_0$ and the current set of points $P_i$.

In 1505, whether the current iteration count i is equal to or less than the maximum number of iterations K may be determined. Operation 1505 may be performed by the judgment subunit 904. In some embodiments, if i is equal to or less than K, the process may proceed to operation 1507. In some embodiments, if i is greater than K, the process may proceed to operation 1525.

In 1507, N sample points may be selected from the current set of points $P_i$. Operation 1507 may be performed by the reference point selection subunit 906. In some embodiments, the N sample points may be selected randomly according to the RANSAC algorithm.

In 1509, the registration parameter $M_i$ may be updated based on the N sample points selected in 1507. Operation 1509 may be performed by the updating subunit 908. In some embodiments, the registration parameter $M_i$ may be updated based on Equation (3) and the N sample points. For example, the registration parameter $M_i$ may be a solution of Equation (3) when mapping data relating to the N sample points is brought into Equation (3).

In 1511, the current set of points $P_i$ may be updated based on the first threshold $T_1$ to obtain a current set of points $P_{i+1}$. Operation 1511 may be performed by the updating subunit 908. In some embodiments, the registration error of each reference point in the current set of points $P_i$ may be determined based on the registration parameter $M_i$ updated in 1509. Then one or more reference points whose registration error is less than the first threshold $T_1$ may be determined. The determined reference points may form the current set of points $P_{i+1}$. For example, if the current set of points $P_i$ includes eight reference points, such as point A, point B, point C, point D, point E, point F, point G, and point H, and the registration errors of points A-F are less than the first threshold $T_1$, then the six reference points A-F may form the current set of points $P_{i+1}$.

In 1513, a point number $N_{Pi}$ of the current set of points $P_{i+1}$ may be determined. Operation 1513 may be performed by the updating subunit 908.

In 1515, the first threshold $T_1$ and/or the second threshold $T_2$ may be updated based on the current set of points $P_{i+1}$. Operation 1515 may be performed by the updating subunit 908. In some embodiments, the first threshold $T_1$ and the second threshold $T_2$ may be updated in each iteration. In some embodiments, the first threshold $T_1$ may be updated according to a median value of registration errors relating to all the reference points in the current set of points $P_{i+1}$. In some embodiments, the second threshold $T_2$ may be updated based on the point number $N_{Pi}$ determined in 1513. For example, the second threshold $T_2$ may be updated based on Equation (4):

$$T_2 = N_{Pi}/2. \quad (4)$$

In 1517, whether the point number $N_{Pi}$ of the current set of points $P_{i+1}$ is greater than the second threshold $T_2$ may be determined. Operation 1517 may be performed by the judgment subunit 904. In some embodiments, if the point number $N_{Pi}$ is greater than the second threshold $T_2$, the process may proceed to operation 1519, otherwise the process may proceed to operation 1518.

In 1518, the current iteration count i may be updated. Operation 1518 may be performed by the updating subunit 908. In some embodiments, the current iteration count i may be added by 1. Then the process may return to operation 1505, and a next iteration may be performed.

In 1519, the registration parameter $M_i$ may be updated based on the current set of points $P_{i+1}$. Operation 1519 may be performed by the updating subunit 908. In some embodiments, the registration parameter $M_i$ may be a solution of Equation (3) when mapping data relating to the current set of points $P_{i+1}$ is brought into Equation (3).

In 1521, a current back-projection error $E_i$ may be determined based on the current set of points $P_{i+1}$. Operation 1521 may be performed by the updating subunit 908. In some embodiments, the current back-projection error $E_i$ may be determined based on registration errors of all the $N_{Pi}$ reference points in the current set of points $P_{i+1}$. For example, the current back-projection error $E_i$ may be a mean square error (MSE) of the $N_{Pi}$ registration errors.

In 1523, whether the current back-projection error $E_i$ is less than a back-projection error $E_{i-1}$ determined in a previous iteration may be determined. Operation 1523 may be performed by the judgment subunit 904. In some embodiments, if the current back-projection error $E_i$ is less than the back-projection error $E_{i-1}$, the process may return to operation 1518, and then the process may return to 1505. Otherwise, the process may proceed to operation 1525.

In 1525, the last updated registration parameter $M_i$ may be designated as a target registration parameter. Operation 1525 may be performed by the registration parameter determination unit 708.

It should be noted that the description of the process 1500 is provided for the purposes of illustration, and not intended to limit the scope of the present disclosure. For persons having ordinary skills in the art, various variations and modifications may be conducted under the teaching of the present disclosure. However, those variations and modifications do not depart from the scope of the present disclosure. For example, operation 1501 and operation 1503 may be integrated into one single operation. As another example, operation 1519 and operation 1521 may be integrated into one single operation. As a further example, operation 1503 may be performed before operation 1501.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and describe.

What is claimed is:

1. A method implemented on at least one device each of which has at least one processor and a storage for registering multi-modality images, the method comprising:

acquiring a first image relating to one or more reference objects;

acquiring a second image relating to the one or more reference objects;

determining a set of reference points based on the one or more reference objects, the set of reference points including a plurality of first reference points, wherein the plurality of first reference points include at least two first reference points, and a distance between the at least two first reference points represents a shortest distance between two portions of the one or more reference objects;

determining a set of mapping data corresponding to the set of reference points in the first image and the second image; and determining one or more registration parameters by comparing a plurality of back-projection errors generated in a plurality of iterations that are performed based on the set of mapping data.

2. The method of claim 1, wherein
the first image is obtained by a first imaging device, and the second image is obtained by a second imaging device; or
the first image is obtained by a first portion of a multi-modality imaging device, and the second image is obtained by a second portion of the multi-modality imaging device.

3. The method of claim 1, wherein the one or more reference objects include a plurality of skew lines on different planes, the plurality of skew lines constituting a registration model.

4. The method of claim 1, further comprising:
determining a plurality of characteristic points of the one or more reference objects;
determining the one or more reference objects in the first image based on the plurality of characteristic points; and
determining the one or more reference objects in the second image based on the plurality of characteristic points.

5. The method of claim 4, wherein the determining a plurality of characteristic points of the one or more reference objects includes:
determining a plurality of intersection points between at least three parallel planes and the one or more reference objects; and
designating the plurality of intersection points as the plurality of characteristic points.

6. The method of claim 4, wherein the determining the one or more reference objects in the first image based on the plurality of characteristic points includes:
acquiring a first plurality of coordinate positions of the plurality of characteristic points in the first image;
determining one or more first slopes corresponding to the one or more reference objects based on the first plurality of coordinate positions; and
determining a first location distribution of the one or more reference objects in the first image based on the one or more first slopes and the first plurality of coordinate positions.

7. The method of claim 6, wherein the determining one or more first slopes corresponding to the one or more reference objects based on the first plurality of coordinate positions includes:
obtaining a first set of slopes by determining at least one slope based on every two of the plurality of characteristic points;
dividing the first set of slopes into a plurality of groups based on values of the first set of slopes, wherein one or more slopes in each group are substantially the same;
determining one or more target groups that have a maximum number of slopes; and
designating one or more values of the one or more target groups as the one or more first slopes corresponding to the one or more reference objects.

8. The method of claim 6, wherein the determining a first location distribution of the one or more reference objects in the first image based on the one or more first slopes and the first plurality of coordinate positions includes:
determining a distance between every two reference objects in the first image; and
determining the first location distribution of the one or more reference objects in the first image based on the distances determined for the one or more reference objects in the first image.

9. The method of claim 4, wherein the determining the one or more reference objects in the second image based on the plurality of characteristic points includes:
acquiring a second plurality of coordinate positions of the plurality of characteristic points in the second image;
determining one or more second slopes corresponding to the one or more reference objects based on the second plurality of coordinate positions; and
determining a second location distribution of the one or more reference objects in the second image based on the one or more second slopes and the second plurality of coordinate positions.

10. The method of claim 9, wherein the determining one or more second slopes corresponding to the one or more reference objects based on the second plurality of coordinate positions includes:
obtaining a second set of slopes by determining at least one slope based on every two of the plurality of characteristic points;
dividing the second set of slopes into a plurality of groups based on values of the second set of slopes, wherein one or more slopes in each group are substantially the same;
determining one or more target groups that have a maximum number of slopes; and
designating one or more values of the one or more target groups as the one or more second slopes corresponding to the one or more reference objects.

11. The method of claim 9, wherein the determining a second location distribution of the one or more reference objects in the second image based on the one or more second slopes and the second plurality of coordinate positions includes:
determining a distance between every two reference objects in the second image; and
determining the second location distribution of the one or more reference objects in the second image based on the distances determined for the one or more reference objects in the second image.

12. The method of claim 1, wherein the set of reference points further includes a plurality of second reference points, the method further comprising:
determining the plurality of second reference points based on the plurality of first reference points, wherein one of the plurality of second reference points and one of the plurality of first reference points that belong to a same reference object of the one or more reference objects have a specific distance.

13. The method of claim 1, wherein the plurality of first reference points includes a first point and a second point, and a distance between the first point and the second point represents the shortest distance between two portions of one of the one or more reference objects.

14. The method of claim 1, wherein the set of mapping data reflect a mapping relation between a first coordinate position of at least one reference point of the set of reference points in the first image and a second coordinate position of the at least one reference point in the second image.

15. The method of claim 1, wherein the one or more registration parameters include a rotation matrix and a translation vector.

16. The method of claim 1, wherein the plurality of iterations are performed based on a Random Sample Consensus algorithm.

17. A system, comprising:
at least one storage device storing a set of instructions; and
at least one processor in communication with the storage device, wherein when executing the set of instructions, the at least one processor is configured to cause the system to perform operations including:
acquire a first image relating to one or more reference objects;
acquire a second image relating to the one or more reference objects;
determine a set of reference points based on the one or more reference objects, the set of reference points including a plurality of first reference points, wherein the plurality of first reference points include at least two first reference points, and a distance between the at least two first reference points represents a shortest distance between two portions of the one or more reference objects;
determine a set of mapping data corresponding to the set of reference points in the first image and the second image; and
determine one or more registration parameters by comparing a plurality of back-projection errors generated in a plurality of iterations that are performed based on the set of mapping data.

18. The system of claim 17, wherein
the first image is obtained by a first imaging device, and the second image is obtained by a second imaging device; or
the first image is obtained by a first portion of a multi-modality imaging device, and the second image is obtained by a second portion of the multi-modality imaging device.

19. The system of claim 17, wherein the one or more reference objects include a plurality of skew lines on different planes, the plurality of skew lines constituting a registration model.

20. A non-transitory computer-readable medium, comprising at least one set of instructions, wherein when executed by at least one processor of a computing device, the at least one set of instructions cause the at least one processor to effectuate a method comprising:
acquiring a first image relating to one or more reference objects;
acquiring a second image relating to the one or more reference objects;
determining a set of reference points based on the one or more reference objects, the set of reference points including a plurality of first reference points, wherein the plurality of first reference points include at least two first reference points, and a distance between the at least two first reference points represents a shortest distance between two portions of the one or more reference objects;
determining a set of mapping data corresponding to the set of reference points in the first image and the second image; and
determining one or more registration parameters by comparing a plurality of back-projection errors generated in a plurality of iterations that are performed based on the set of mapping data.

* * * * *